United States Patent [19]
Varshavsky et al.

[11] Patent Number: 5,861,312
[45] Date of Patent: Jan. 19, 1999

[54] NUCLEIC ACID ENCODING MAMMALIAN UBR1

[75] Inventors: Alexander Varshavsky, La Canada Flintridge; Yong Tae Kwon, Pasadena, both of Calif.

[73] Assignee: California Institute of Technology, Pasadena, Calif.

[21] Appl. No.: 982,956

[22] Filed: Dec. 2, 1997

[51] Int. Cl.⁶ .......................... C12N 15/12; C12N 15/63; C12N 5/10; C12N 1/21
[52] U.S. Cl. .................. 435/325; 435/320.1; 435/252.3; 536/23.5
[58] Field of Search ..................... 536/23.5; 435/320.1, 435/325, 252.3

[56] References Cited

PUBLICATIONS

Bachmair et al., *Science* 234: 179–186 (1986).
Solomon et al., *J. Biol. Chem.* 271: 26690–26697 (1996).
Price et al., Abstracts from 1997 FASEB Summer Meeting, Vermont: A988 (abstract 772) (1997).
Reiss and Hershko, *J. Biol. Chem.* 265: 3685–3690 (1990).
Hershko et al., *Annu. Rev. Biochem.* 61: 761–807 (1992).
Bartel et al., *EMBO J. 9:* 3179–3189 (1990).
Baker et al., *PNAS USA 88:* 1090–1094 (1991).
Madura et al., *J. Biol. Chem. 268:* 12046–12054 (1993).
Varshavsky et al., *Cold Spring Harbor Symp. Quent. Biol. 60:* 461–478 (1996).

*Primary Examiner*—Nancy Degen
*Assistant Examiner*—John S. Brusca
*Attorney, Agent, or Firm*—Kevin M. Farrell

[57] ABSTRACT

Disclosed here is a nucleic acid sequence encoding a recognition component of the N-end rule pathway. This nucleic acid sequence is characterized by the ability to specifically hybridize to the nucleic acid sequence of SEQ ID NO 1 under stringent hybridization conditions. Such conditions are defined below. Also disclosed is a nucleic acid sequence encoding a recognition component of the N-end rule pathway which is characterized by the ability to specifically hybridize to the nucleic acid sequence of SEQ ID NO 2 under stringent hybridization conditions. Also disclosed are DNA expression vectors containing nucleic acid sequences of the type described above, as well as cells transformed with such expression vectors. Further disclosed are applications for the compositions described above.

10 Claims, 1 Drawing Sheet

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 6395 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 115..5385

( x i ) SEQUENCE DESCRIPTION: SEQ ID NO:1:

```
CCTGACTTTC AGGGGCCGTC GTAAAAGTGT CGTCCCTGTC GCGTCGGGCC GGCCACAGGT           60

TTCCGCTAGC TGGCGGCCGG GGGTCGGGAA CTGCGGGCGT TCGTTTCCCT TAAG ATG            117
                                                             Met
                                                              1

GCG GAC GAA GAG ATG GAC GGC GCC GAG AGG ATG GAC GTC AGC CCG GAG            165
Ala Asp Glu Glu Met Asp Gly Ala Glu Arg Met Asp Val Ser Pro Glu
             5                  10                  15

CCT CCC CTG GCC CCG CAG CGG CCG GCA TCG TGG TGG GAT CAG CAA GTT            213
Pro Pro Leu Ala Pro Gln Arg Pro Ala Ser Trp Trp Asp Gln Gln Val
         20                  25                  30

GAT TTC TAT ACT GCT TTC TTA CAT CAT TTG GCA CAA TTA GTG CCA GAA            261
Asp Phe Tyr Thr Ala Phe Leu His His Leu Ala Gln Leu Val Pro Glu
     35                  40                  45

ATT TAT TTT GCT GAG ATG GAC CCA GAT TTG GAA AAG CAA GAA GAG AGT            309
Ile Tyr Phe Ala Glu Met Asp Pro Asp Leu Glu Lys Gln Glu Glu Ser
 50                  55                  60                  65

GTA CAG ATG TCA ATA CTC ACT CCT TTG GAG TGG TAC TTA TTT GGA GAG            357
Val Gln Met Ser Ile Leu Thr Pro Leu Glu Trp Tyr Leu Phe Gly Glu
                 70                  75                  80

GAT CCG GAT ATT TGC TTA GAG AAA TTA AAA CAC AGT GGA GCG TTC CAG            405
Asp Pro Asp Ile Cys Leu Glu Lys Leu Lys His Ser Gly Ala Phe Gln
             85                  90                  95

TTG TGT GGG AAG GTT TTC AAA AGT GGA GAA ACA ACA TAT TCC TGT AGG            453
Leu Cys Gly Lys Val Phe Lys Ser Gly Glu Thr Thr Tyr Ser Cys Arg
        100                 105                 110

GAT TGT GCA ATT GAT CCA ACG TGT GTG CTC TGT ATG GAC TGC TTC CAA            501
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Asp | Cys | Ala | Ile | Asp | Pro | Thr | Cys | Val | Leu | Cys | Met | Asp | Cys | Phe | Gln |      |
|     | 115 |     |     |     | 120 |     |     |     |     | 125 |     |     |     |     |     |      |
| AGT | AGT | GTT | CAT | AAA | AAC | CAT | CGT | TAC | AAG | ATG | CAT | ACT | TCT | ACT | GGA | 549  |
| Ser | Ser | Val | His | Lys | Asn | His | Arg | Tyr | Lys | Met | His | Thr | Ser | Thr | Gly |      |
| 130 |     |     |     |     | 135 |     |     |     | 140 |     |     |     |     |     | 145 |      |
| GGG | GGC | TTC | TGT | GAC | TGT | GGA | GAC | ACA | GAA | GCG | TGG | AAA | ACT | GGC | CCT | 597  |
| Gly | Gly | Phe | Cys | Asp | Cys | Gly | Asp | Thr | Glu | Ala | Trp | Lys | Thr | Gly | Pro |      |
|     |     |     |     | 150 |     |     |     |     | 155 |     |     |     |     |     | 160 |      |
| TTT | TGT | GTG | GAT | CAC | GAG | CCT | GGA | AGA | GCA | GGT | ACT | ACA | AAA | GAG | AGC | 645  |
| Phe | Cys | Val | Asp | His | Glu | Pro | Gly | Arg | Ala | Gly | Thr | Thr | Lys | Glu | Ser |      |
|     |     |     | 165 |     |     |     |     | 170 |     |     |     |     | 175 |     |     |      |
| TTA | CAT | TGC | CCA | TTG | AAT | GAA | GAG | GTG | ATT | GCT | CAA | GCC | AGG | AGA | ATA | 693  |
| Leu | His | Cys | Pro | Leu | Asn | Glu | Glu | Val | Ile | Ala | Gln | Ala | Arg | Arg | Ile |      |
|     |     | 180 |     |     |     |     | 185 |     |     |     |     | 190 |     |     |     |      |
| TTC | CCT | TCG | GTG | ATA | AAA | TAC | ATT | GTA | GAA | ATG | ACT | ATA | TGG | GAA | GAA | 741  |
| Phe | Pro | Ser | Val | Ile | Lys | Tyr | Ile | Val | Glu | Met | Thr | Ile | Trp | Glu | Glu |      |
|     | 195 |     |     |     |     | 200 |     |     |     |     | 205 |     |     |     |     |      |
| GAA | AAG | GAA | TTG | CCT | CCT | GAA | CTG | CAG | ATA | AGG | GAG | AAA | AAT | GAA | CGA | 789  |
| Glu | Lys | Glu | Leu | Pro | Pro | Glu | Leu | Gln | Ile | Arg | Glu | Lys | Asn | Glu | Arg |      |
| 210 |     |     |     |     | 215 |     |     |     |     | 220 |     |     |     |     | 225 |      |
| TAC | TAT | TGT | GTC | CTT | TTC | AAC | GAT | GAG | CAC | CAT | TCG | TAT | GAT | CAT | GTG | 837  |
| Tyr | Tyr | Cys | Val | Leu | Phe | Asn | Asp | Glu | His | His | Ser | Tyr | Asp | His | Val |      |
|     |     |     |     | 230 |     |     |     |     | 235 |     |     |     |     |     | 240 |      |
| ATC | TAC | AGT | CTG | CAG | AGA | GCT | CTA | GAT | TGC | GAG | CTT | GCA | GAG | GCA | CAG | 885  |
| Ile | Tyr | Ser | Leu | Gln | Arg | Ala | Leu | Asp | Cys | Glu | Leu | Ala | Glu | Ala | Gln |      |
|     |     |     | 245 |     |     |     |     | 250 |     |     |     |     | 255 |     |     |      |
| CTG | CAC | ACG | ACT | GCC | ATC | GAC | AAA | GAG | GGT | CGC | CGG | GCT | GTC | AAA | GCA | 933  |
| Leu | His | Thr | Thr | Ala | Ile | Asp | Lys | Glu | Gly | Arg | Arg | Ala | Val | Lys | Ala |      |
|     |     | 260 |     |     |     |     | 265 |     |     |     |     | 270 |     |     |     |      |
| GGT | GTG | TAT | GCC | ACT | TGC | CAG | GAA | GCA | AAG | GAG | GAT | ATA | AAG | AGT | CAC | 981  |
| Gly | Val | Tyr | Ala | Thr | Cys | Gln | Glu | Ala | Lys | Glu | Asp | Ile | Lys | Ser | His |      |
|     | 275 |     |     |     |     | 280 |     |     |     |     | 285 |     |     |     |     |      |
| TCA | GAG | AAC | GTC | TCT | CAG | CAC | CCC | CTC | CAT | GTG | GAA | GTG | CTG | CAC | TCC | 1029 |
| Ser | Glu | Asn | Val | Ser | Gln | His | Pro | Leu | His | Val | Glu | Val | Leu | His | Ser |      |
| 290 |     |     |     |     | 295 |     |     |     |     | 300 |     |     |     |     | 305 |      |
| GTG | GTT | ATG | GCT | CAC | CAG | AAA | TTC | GCT | CTG | CGC | CTT | GGC | TCC | TGG | ATG | 1077 |
| Val | Val | Met | Ala | His | Gln | Lys | Phe | Ala | Leu | Arg | Leu | Gly | Ser | Trp | Met |      |
|     |     |     |     | 310 |     |     |     |     | 315 |     |     |     |     |     | 320 |      |
| AAC | AAA | ATT | ATG | AGC | TAT | TCA | AGT | GAC | TTT | AGA | CAG | ATA | TTT | TGC | CAG | 1125 |
| Asn | Lys | Ile | Met | Ser | Tyr | Ser | Ser | Asp | Phe | Arg | Gln | Ile | Phe | Cys | Gln |      |
|     |     |     | 325 |     |     |     |     | 330 |     |     |     |     | 335 |     |     |      |
| GCC | TGC | CTC | GTA | GAA | GAA | CCT | GGC | TCT | GAA | AAT | CCC | TGT | CTT | ATA | AGC | 1173 |
| Ala | Cys | Leu | Val | Glu | Glu | Pro | Gly | Ser | Glu | Asn | Pro | Cys | Leu | Ile | Ser |      |
|     |     | 340 |     |     |     |     | 345 |     |     |     |     | 350 |     |     |     |      |
| AGA | CTA | ATG | CTT | TGG | GAT | GCA | AAA | CTT | TAT | AAA | GGT | GCC | CGT | AAG | ATC | 1221 |
| Arg | Leu | Met | Leu | Trp | Asp | Ala | Lys | Leu | Tyr | Lys | Gly | Ala | Arg | Lys | Ile |      |
|     | 355 |     |     |     |     | 360 |     |     |     |     | 365 |     |     |     |     |      |
| CTT | CAT | GAA | TTG | ATC | TTT | AGT | AGT | TTT | TTT | ATG | GAG | ATG | GAA | TAC | AAA | 1269 |
| Leu | His | Glu | Leu | Ile | Phe | Ser | Ser | Phe | Phe | Met | Glu | Met | Glu | Tyr | Lys |      |
| 370 |     |     |     |     | 375 |     |     |     |     | 380 |     |     |     |     | 385 |      |
| AAA | CTC | TTT | GCT | ATG | GAA | TTT | GTG | AAG | TAT | TAT | AAA | CAA | CTG | CAG | AAA | 1317 |
| Lys | Leu | Phe | Ala | Met | Glu | Phe | Val | Lys | Tyr | Tyr | Lys | Gln | Leu | Gln | Lys |      |
|     |     |     |     | 390 |     |     |     |     | 395 |     |     |     |     | 400 |     |      |
| GAG | TAC | ATC | AGC | GAC | GAC | CAC | GAG | AGA | AGC | ATC | TCC | ATA | ACC | GCC | CTG | 1365 |
| Glu | Tyr | Ile | Ser | Asp | Asp | His | Glu | Arg | Ser | Ile | Ser | Ile | Thr | Ala | Leu |      |
|     |     |     | 405 |     |     |     |     | 410 |     |     |     |     | 415 |     |     |      |
| TCC | GTG | CAG | ATG | CTC | ACC | GTC | CCG | ACC | TTG | GCC | CGG | CAT | CTT | ATT | GAA | 1413 |
| Ser | Val | Gln | Met | Leu | Thr | Val | Pro | Thr | Leu | Ala | Arg | His | Leu | Ile | Glu |      |
|     |     | 420 |     |     |     |     | 425 |     |     |     |     | 430 |     |     |     |      |
| GAG | CAG | AAT | GTT | ATT | TCT | GTC | ATT | ACT | GAA | ACG | CTG | CTA | GAA | GTT | TTA | 1461 |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Glu | Gln | Asn | Val | Ile | Ser | Val | Ile | Thr | Glu | Thr | Leu | Leu | Glu | Val | Leu |      |
|     | 435 |     |     |     | 440 |     |     |     |     | 445 |     |     |     |     |     |      |
| CCT | GAA | TAC | TTG | GAC | AGG | AAC | AAT | AAA | TTC | AAC | TTC | CAG | GGT | TAT | AGC | 1509 |
| Pro | Glu | Tyr | Leu | Asp | Arg | Asn | Asn | Lys | Phe | Asn | Phe | Gln | Gly | Tyr | Ser |      |
| 450 |     |     |     |     | 455 |     |     |     | 460 |     |     |     |     |     | 465 |      |
| CAG | GAC | AAA | CTG | GGA | AGA | GTC | TAC | GCA | GTT | ATA | TGT | GAC | CTA | AAG | TAT | 1557 |
| Gln | Asp | Lys | Leu | Gly | Arg | Val | Tyr | Ala | Val | Ile | Cys | Asp | Leu | Lys | Tyr |      |
|     |     |     |     | 470 |     |     |     |     | 475 |     |     |     |     | 480 |     |      |
| ATC | CTG | ATT | AGC | AAG | CCT | GTC | ATA | TGG | ACA | GAA | CGA | TTA | AGA | GCG | CAG | 1605 |
| Ile | Leu | Ile | Ser | Lys | Pro | Val | Ile | Trp | Thr | Glu | Arg | Leu | Arg | Ala | Gln |      |
|     |     |     | 485 |     |     |     |     | 490 |     |     |     |     | 495 |     |     |      |
| TTC | CTG | GAA | GGT | TTC | CGG | TCT | TTT | CTG | AAG | ATT | CTT | ACC | TGT | ATG | CAG | 1653 |
| Phe | Leu | Glu | Gly | Phe | Arg | Ser | Phe | Leu | Lys | Ile | Leu | Thr | Cys | Met | Gln |      |
|     |     | 500 |     |     |     |     | 505 |     |     |     |     | 510 |     |     |     |      |
| GGA | ATG | GAA | GAA | ATC | AGA | AGA | CAA | GTT | GGA | CAA | CAC | ATT | GAA | GTG | GAC | 1701 |
| Gly | Met | Glu | Glu | Ile | Arg | Arg | Gln | Val | Gly | Gln | His | Ile | Glu | Val | Asp |      |
|     | 515 |     |     |     |     | 520 |     |     |     |     | 525 |     |     |     |     |      |
| CCT | GAC | TGG | GAG | GCT | GCC | ATC | GCT | ATA | CAG | ATG | CAA | CTA | AAG | AAT | ATT | 1749 |
| Pro | Asp | Trp | Glu | Ala | Ala | Ile | Ala | Ile | Gln | Met | Gln | Leu | Lys | Asn | Ile |      |
| 530 |     |     |     |     | 535 |     |     |     |     | 540 |     |     |     |     | 545 |      |
| TTG | CTC | ATG | TTC | CAA | GAG | TGG | TGT | GCT | TGT | GAT | GAA | GAT | CTC | TTA | CTG | 1797 |
| Leu | Leu | Met | Phe | Gln | Glu | Trp | Cys | Ala | Cys | Asp | Glu | Asp | Leu | Leu | Leu |      |
|     |     |     |     | 550 |     |     |     | 555 |     |     |     |     | 560 |     |     |      |
| GTG | GCT | TAT | AAA | GAA | TGT | CAC | AAA | GCT | GTA | ATG | AGG | TGC | AGT | ACA | AAT | 1845 |
| Val | Ala | Tyr | Lys | Glu | Cys | His | Lys | Ala | Val | Met | Arg | Cys | Ser | Thr | Asn |      |
|     |     |     | 565 |     |     |     |     | 570 |     |     |     |     | 575 |     |     |      |
| TTC | ATG | TCC | AGT | ACC | AAG | ACA | GTA | GTG | CAA | TTG | TGC | GGT | CAT | AGT | CTG | 1893 |
| Phe | Met | Ser | Ser | Thr | Lys | Thr | Val | Val | Gln | Leu | Cys | Gly | His | Ser | Leu |      |
|     |     | 580 |     |     |     |     | 585 |     |     |     |     | 590 |     |     |     |      |
| GAA | ACC | AAA | TCC | TAC | AAA | GTG | TCT | GAG | GAC | CTT | GTA | AGC | ATA | CAC | CTG | 1941 |
| Glu | Thr | Lys | Ser | Tyr | Lys | Val | Ser | Glu | Asp | Leu | Val | Ser | Ile | His | Leu |      |
|     | 595 |     |     |     |     | 600 |     |     |     |     | 605 |     |     |     |     |      |
| CCA | CTC | TCT | AGA | ACA | CTT | GCT | GGT | CTT | CAT | GTA | CGT | TTA | AGC | AGA | CTA | 1989 |
| Pro | Leu | Ser | Arg | Thr | Leu | Ala | Gly | Leu | His | Val | Arg | Leu | Ser | Arg | Leu |      |
| 610 |     |     |     |     | 615 |     |     |     |     | 620 |     |     |     |     | 625 |      |
| GGT | GCT | ATT | TCA | AGA | CTG | CAT | GAA | TTT | GTG | CCT | TTT | GAC | AGC | TTT | CAA | 2037 |
| Gly | Ala | Ile | Ser | Arg | Leu | His | Glu | Phe | Val | Pro | Phe | Asp | Ser | Phe | Gln |      |
|     |     |     |     | 630 |     |     |     |     | 635 |     |     |     |     | 640 |     |      |
| GTA | GAG | GTC | CTG | GTG | GAG | TAC | CCG | CTG | CGC | TGC | CTG | GTC | CTG | GTG | GCT | 2085 |
| Val | Glu | Val | Leu | Val | Glu | Tyr | Pro | Leu | Arg | Cys | Leu | Val | Leu | Val | Ala |      |
|     |     |     | 645 |     |     |     |     | 650 |     |     |     |     | 655 |     |     |      |
| CAG | GTT | GTT | GCT | GAG | ATG | TGG | CGA | AGA | AAC | GGG | CTC | TCA | CTC | ATC | AGC | 2133 |
| Gln | Val | Val | Ala | Glu | Met | Trp | Arg | Arg | Asn | Gly | Leu | Ser | Leu | Ile | Ser |      |
|     |     | 660 |     |     |     |     | 665 |     |     |     |     | 670 |     |     |     |      |
| CAG | GTT | TTC | TAT | TAT | CAA | GAT | GTT | AAA | TGC | AGG | GAG | GAA | ATG | TAC | GAT | 2181 |
| Gln | Val | Phe | Tyr | Tyr | Gln | Asp | Val | Lys | Cys | Arg | Glu | Glu | Met | Tyr | Asp |      |
|     | 675 |     |     |     |     | 680 |     |     |     |     | 685 |     |     |     |     |      |
| AAA | GAT | ATC | ATC | ATG | CTT | CAG | ATT | GGA | GCA | TCT | ATA | ATG | GAT | CCC | AAC | 2229 |
| Lys | Asp | Ile | Ile | Met | Leu | Gln | Ile | Gly | Ala | Ser | Ile | Met | Asp | Pro | Asn |      |
| 690 |     |     |     |     | 695 |     |     |     |     | 700 |     |     |     |     | 705 |      |
| AAG | TTC | TTG | TTA | CTG | GTA | CTT | CAG | AGA | TAT | GAA | CTT | ACT | GAT | GCT | TTT | 2277 |
| Lys | Phe | Leu | Leu | Leu | Val | Leu | Gln | Arg | Tyr | Glu | Leu | Thr | Asp | Ala | Phe |      |
|     |     |     |     | 710 |     |     |     |     | 715 |     |     |     |     | 720 |     |      |
| AAC | AAG | ACC | ATA | TCC | ACA | AAA | GAC | CAG | GAT | TTG | ATT | AAA | CAG | TAT | AAT | 2325 |
| Asn | Lys | Thr | Ile | Ser | Thr | Lys | Asp | Gln | Asp | Leu | Ile | Lys | Gln | Tyr | Asn |      |
|     |     |     | 725 |     |     |     |     | 730 |     |     |     |     | 735 |     |     |      |
| ACA | TTA | ATA | GAA | GAA | ATG | CTT | CAG | GTC | CTC | ATC | TAT | ATT | GTG | GGA | GAA | 2373 |
| Thr | Leu | Ile | Glu | Glu | Met | Leu | Gln | Val | Leu | Ile | Tyr | Ile | Val | Gly | Glu |      |
|     |     | 740 |     |     |     |     | 745 |     |     |     |     | 750 |     |     |     |      |
| CGT | TAT | GTA | CCT | GGA | GTG | GGA | AAT | GTT | ACC | AGA | GAG | GAG | GTT | ATA | ATG | 2421 |

```
                Arg  Tyr  Val  Pro  Gly  Val  Gly  Asn  Val  Thr  Arg  Glu  Glu  Val  Ile  Met
                     755                 760                 765

AGA  GAG  ATT  ACT  CAC  TTA  CTT  TGC  ATT  GAG  CCC  ATG  CCA  CAC  AGT  GCC                  2469
Arg  Glu  Ile  Thr  His  Leu  Leu  Cys  Ile  Glu  Pro  Met  Pro  His  Ser  Ala
770                 775                 780                           785

ATC  GCC  AGA  AAC  CTA  CCT  GAG  AAC  GAA  AAT  AAT  GAA  ACT  GGC  TTA  GAG                  2517
Ile  Ala  Arg  Asn  Leu  Pro  Glu  Asn  Glu  Asn  Asn  Glu  Thr  Gly  Leu  Glu
                    790                 795                           800

AAT  GTC  ATA  AAC  AAA  GTG  GCC  ACA  TTT  AAG  AAA  CCA  GGT  GTG  TCG  GGC                  2565
Asn  Val  Ile  Asn  Lys  Val  Ala  Thr  Phe  Lys  Lys  Pro  Gly  Val  Ser  Gly
               805                 810                      815

CAT  GGA  GTT  TAT  GAA  TTG  AAA  GAT  GAA  TCA  CTG  AAA  GAC  TTC  AAT  ATG                  2613
His  Gly  Val  Tyr  Glu  Leu  Lys  Asp  Glu  Ser  Leu  Lys  Asp  Phe  Asn  Met
          820                 825                      830

TAC  TTT  TAC  CAT  TAT  TCT  AAA  ACA  CAG  CAT  AGC  AAG  GCT  GAA  CAT  ATG                  2661
Tyr  Phe  Tyr  His  Tyr  Ser  Lys  Thr  Gln  His  Ser  Lys  Ala  Glu  His  Met
     835                 840                      845

CAG  AAG  AAA  AGG  AGA  AAA  CAA  GAA  AAT  AAA  GAT  GAA  GCA  TTG  CCG  CCG                  2709
Gln  Lys  Lys  Arg  Arg  Lys  Gln  Glu  Asn  Lys  Asp  Glu  Ala  Leu  Pro  Pro
850                 855                      860                      865

CCA  CCT  CCT  CCA  GAG  TTC  TGC  CCT  GCT  TTC  AGC  AAA  GTA  GTC  AAC  CTG                  2757
Pro  Pro  Pro  Pro  Glu  Phe  Cys  Pro  Ala  Phe  Ser  Lys  Val  Val  Asn  Leu
                    870                 875                      880

CTC  AGC  TGT  GAT  GTT  ATG  ATA  TAC  ATC  CTC  AGG  ACC  ATC  TTT  GAG  CGG                  2805
Leu  Ser  Cys  Asp  Val  Met  Ile  Tyr  Ile  Leu  Arg  Thr  Ile  Phe  Glu  Arg
               885                 890                      895

GCA  GTG  GAC  ACG  GAG  TCT  AAT  CTG  TGG  ACA  GAA  GGG  ATG  CTG  CAG  ATG                  2853
Ala  Val  Asp  Thr  Glu  Ser  Asn  Leu  Trp  Thr  Glu  Gly  Met  Leu  Gln  Met
          900                 905                      910

GCG  TTC  CAT  ATA  TTG  GCA  CTG  GGC  TTG  CTG  GAA  GAG  AAG  CAG  CAG  CTT                  2901
Ala  Phe  His  Ile  Leu  Ala  Leu  Gly  Leu  Leu  Glu  Glu  Lys  Gln  Gln  Leu
     915                 920                      925

CAG  AAA  GCT  CCT  GAA  GAG  GAA  GTG  GCT  TTT  GAC  TTT  TAC  CAT  AAA  GCT                  2949
Gln  Lys  Ala  Pro  Glu  Glu  Glu  Val  Ala  Phe  Asp  Phe  Tyr  His  Lys  Ala
930                 935                      940                      945

TCA  AGA  TTG  GGA  AGT  TCA  GCC  ATG  AAT  GCT  CAG  AAT  ATA  CAA  ATG  CTC                  2997
Ser  Arg  Leu  Gly  Ser  Ser  Ala  Met  Asn  Ala  Gln  Asn  Ile  Gln  Met  Leu
                    950                 955                      960

TTG  GAA  AGA  CTC  AAA  GGA  ATC  CCC  CAA  TTA  GAA  GGC  CAG  AAG  GAC  ATG                  3045
Leu  Glu  Arg  Leu  Lys  Gly  Ile  Pro  Gln  Leu  Glu  Gly  Gln  Lys  Asp  Met
               965                 970                      975

ATA  ACA  TGG  ATA  CTC  CAG  ATG  TTT  GAC  ACA  GTG  AAG  CGA  TTA  AGA  GAA                  3093
Ile  Thr  Trp  Ile  Leu  Gln  Met  Phe  Asp  Thr  Val  Lys  Arg  Leu  Arg  Glu
          980                 985                      990

AAA  TCT  TGT  TTA  GTT  GTG  GCA  ACC  ACT  TCA  GGA  CTG  GAG  TGC  ATT  AAG                  3141
Lys  Ser  Cys  Leu  Val  Val  Ala  Thr  Thr  Ser  Gly  Leu  Glu  Cys  Ile  Lys
     995                 1000                     1005

AGT  GAG  GAG  ATT  ACT  CAT  GAT  AAA  GAA  AAG  GCA  GAA  CGG  AAG  AGA  AAA                  3189
Ser  Glu  Glu  Ile  Thr  His  Asp  Lys  Glu  Lys  Ala  Glu  Arg  Lys  Arg  Lys
1010                1015                     1020                     1025

GCT  GAG  GCC  GCT  AGG  CTT  CAT  CGC  CAG  AAG  ATC  ATG  GCC  CAG  ATG  TCT                  3237
Ala  Glu  Ala  Ala  Arg  Leu  His  Arg  Gln  Lys  Ile  Met  Ala  Gln  Met  Ser
                    1030                1035                     1040

GCC  TTA  CAG  AAA  AAC  TTC  ATT  GAA  ACC  CAC  AAA  CTC  ATG  TAT  GAT  AAT                  3285
Ala  Leu  Gln  Lys  Asn  Phe  Ile  Glu  Thr  His  Lys  Leu  Met  Tyr  Asp  Asn
               1045                1050                     1055

ACG  TCA  GAA  GTA  ACA  GGG  AAG  GAA  GAC  TCC  ATT  ATG  GAG  GAA  GAG  AGC                  3333
Thr  Ser  Glu  Val  Thr  Gly  Lys  Glu  Asp  Ser  Ile  Met  Glu  Glu  Glu  Ser
          1060                1065                     1070

ACC  TCA  GCA  GTC  AGT  GAG  GCC  TCT  AGA  ATT  GCT  CTG  GGC  CCT  AAA  CGG                  3381
```

```
    Thr Ser Ala Val Ser Glu Ala Ser Arg Ile Ala Leu Gly Pro Lys Arg
        1075                1080                1085

GGC CCG GCT GTT ACC GAA AAG GAG GTG CTG ACG TGC ATC CTC TGC CAA         3429
Gly Pro Ala Val Thr Glu Lys Glu Val Leu Thr Cys Ile Leu Cys Gln
1090                1095                1100                1105

GAA GAA CAA GAG GTA AAA CTA GAA AAT AAT GCC ATG GTA TTG TCA GCA         3477
Glu Glu Gln Glu Val Lys Leu Glu Asn Asn Ala Met Val Leu Ser Ala
                    1110                1115                1120

TGT GTG CAG AAA TCC ACC GCC CTA ACC CAG CAC AGA GGG AAG CCT GTG         3525
Cys Val Gln Lys Ser Thr Ala Leu Thr Gln His Arg Gly Lys Pro Val
            1125                1130                1135

GAC CAC TTA GGG GAA ACA CTG GAC CCT CTT TTC ATG GAT CCA GAC TTG         3573
Asp His Leu Gly Glu Thr Leu Asp Pro Leu Phe Met Asp Pro Asp Leu
                1140                1145                1150

GCA CAT GGA ACT TAT ACA GGA AGC TGT GGT CAT GTA ATG CAT GCA GTG         3621
Ala His Gly Thr Tyr Thr Gly Ser Cys Gly His Val Met His Ala Val
        1155                1160                1165

TGC TGG CAG AAG TAT TTT GAA GCT GTG CAG CTG AGC TCG CAG CAG CGC         3669
Cys Trp Gln Lys Tyr Phe Glu Ala Val Gln Leu Ser Ser Gln Gln Arg
1170                1175                1180                1185

ATT CAC GTA GAC CTG TTT GAC CTG GAG AGC GGC GAG TAC CTA TGC CCG         3717
Ile His Val Asp Leu Phe Asp Leu Glu Ser Gly Glu Tyr Leu Cys Pro
                    1190                1195                1200

CTC TGC AAG TCT CTC TGC AAC ACT GTC ATC CCC ATC ATC CCT TTG CAG         3765
Leu Cys Lys Ser Leu Cys Asn Thr Val Ile Pro Ile Ile Pro Leu Gln
            1205                1210                1215

CCG CAG AAG ATC AAC AGT GAG AAT GCG GAG GCT CTT GCT CAA CTT TTG         3813
Pro Gln Lys Ile Asn Ser Glu Asn Ala Glu Ala Leu Ala Gln Leu Leu
                1220                1225                1230

ACC TTG GCC CGG TGG ATA CAG ACT GTC CTT GCC AGA ATA TCG GGT TAT         3861
Thr Leu Ala Arg Trp Ile Gln Thr Val Leu Ala Arg Ile Ser Gly Tyr
        1235                1240                1245

AAT ATA AAG CAT GCT AAA GGA GAA GCC CCA GCA GTT CCT GTC TTG TTT         3909
Asn Ile Lys His Ala Lys Gly Glu Ala Pro Ala Val Pro Val Leu Phe
1250                1255                1260                1265

AAT CAA GGA ATG GGG GAT TCA ACT TTT GAG TTT CAT TCC ATC CTG AGT         3957
Asn Gln Gly Met Gly Asp Ser Thr Phe Glu Phe His Ser Ile Leu Ser
                    1270                1275                1280

TTT GGA GTT CAG TCT TCG GTG AAA TAT TCA AAT AGT ATC AAG GAA ATG         4005
Phe Gly Val Gln Ser Ser Val Lys Tyr Ser Asn Ser Ile Lys Glu Met
            1285                1290                1295

GTC ATT CTC TTC GCC ACA ACA ATT TAC AGA ATT GGC CTG AAA GTG CCT         4053
Val Ile Leu Phe Ala Thr Thr Ile Tyr Arg Ile Gly Leu Lys Val Pro
                1300                1305                1310

CCT GAT GAA CTA GAC CCA CGA GTG CCC ATG ATG ACC TGG AGC ACG TGT         4101
Pro Asp Glu Leu Asp Pro Arg Val Pro Met Met Thr Trp Ser Thr Cys
        1315                1320                1325

GCG TTC ACC ATC CAG GCA ATC GAA AAC CTG TTG GGA GAT GAA GGA AAA         4149
Ala Phe Thr Ile Gln Ala Ile Glu Asn Leu Leu Gly Asp Glu Gly Lys
1330                1335                1340                1345

CCT CTA TTT GGA GCA CTT CAA AAT AGA CAG CAT AGC GGT CTG AAG GCG         4197
Pro Leu Phe Gly Ala Leu Gln Asn Arg Gln His Ser Gly Leu Lys Ala
                    1350                1355                1360

CTA ATG CAG TTT GCA GTT GCA CAG AGG GCT ACC TGC CCT CAG GTC CTG         4245
Leu Met Gln Phe Ala Val Ala Gln Arg Ala Thr Cys Pro Gln Val Leu
            1365                1370                1375

ATA CAC AAA CAT CTG GCT CGG CTC CTG TCA GTT ATT CTT CCT AAC CTG         4293
Ile His Lys His Leu Ala Arg Leu Leu Ser Val Ile Leu Pro Asn Leu
                1380                1385                1390

CAA TCA GAA AAT ACA CCA GGC CTT CTG TCT GTG GAT CTC TTC CAT GTT         4341
```

```
                    Gln  Ser  Glu  Asn  Thr  Pro  Gly  Leu  Leu  Ser  Val  Asp  Leu  Phe  His  Val
                         1395                     1400                     1405

CTG  GTC  GGC  GCA  GTC  TTA  GCG  TTC  CCA  TCC  TTG  TAT  TGG  GAT  GAC  ACC                      4389
Leu  Val  Gly  Ala  Val  Leu  Ala  Phe  Pro  Ser  Leu  Tyr  Trp  Asp  Asp  Thr
1410                1415                     1420                          1425

GTG  GAT  CTG  CAG  CCG  TCG  CCA  CTT  AGT  TCT  TCA  TAT  AAC  CAC  CTC  TAT                      4437
Val  Asp  Leu  Gln  Pro  Ser  Pro  Leu  Ser  Ser  Ser  Tyr  Asn  His  Leu  Tyr
                1430                     1435                          1440

CTC  TTC  CAT  CTG  ATC  ACC  ATG  GCG  CAC  ATG  CTT  CAG  ATA  CTC  CTT  ACA                      4485
Leu  Phe  His  Leu  Ile  Thr  Met  Ala  His  Met  Leu  Gln  Ile  Leu  Leu  Thr
               1445                     1450                     1455

ACA  GAT  ACA  GAT  CTG  TCT  CCA  GGG  CCG  CCG  CTT  GCT  GAG  GGT  GAA  GAG                      4533
Thr  Asp  Thr  Asp  Leu  Ser  Pro  Gly  Pro  Pro  Leu  Ala  Glu  Gly  Glu  Glu
          1460                     1465                     1470

GAT  AGT  GAG  GAG  GCT  CGC  TGT  GCA  TCT  GCT  TTC  TTT  GTG  GAA  GTG  TCG                      4581
Asp  Ser  Glu  Glu  Ala  Arg  Cys  Ala  Ser  Ala  Phe  Phe  Val  Glu  Val  Ser
1475                     1480                     1485

CAG  CAC  ACA  GAC  GGC  CTC  ACT  GGG  TGC  GGT  GCT  CCC  GGC  TGG  TAC  CTG                      4629
Gln  His  Thr  Asp  Gly  Leu  Thr  Gly  Cys  Gly  Ala  Pro  Gly  Trp  Tyr  Leu
1490                     1495                     1500                          1505

TGG  CTC  TCC  CTG  AGG  AAC  GGC  ATC  ACC  CCT  TAC  CTC  CGC  TGT  GCT  GCA                      4677
Trp  Leu  Ser  Leu  Arg  Asn  Gly  Ile  Thr  Pro  Tyr  Leu  Arg  Cys  Ala  Ala
                    1510                     1515                     1520

CTG  CTT  TTC  CAC  TAT  TTA  CTT  GGA  GTA  GCT  CCG  CCT  GAA  GAA  CTG  TTT                      4725
Leu  Leu  Phe  His  Tyr  Leu  Leu  Gly  Val  Ala  Pro  Pro  Glu  Glu  Leu  Phe
               1525                     1530                     1535

GCC  AAT  TCT  GCT  GAA  GGA  GAA  TTC  AGT  GCA  CTC  TGT  AGC  TAT  CTA  TCT                      4773
Ala  Asn  Ser  Ala  Glu  Gly  Glu  Phe  Ser  Ala  Leu  Cys  Ser  Tyr  Leu  Ser
          1540                     1545                     1550

TTA  CCC  ACA  AAT  TTG  TTC  CTG  CTT  TTC  CAG  GAA  TAT  TGG  GAT  ACC  ATA                      4821
Leu  Pro  Thr  Asn  Leu  Phe  Leu  Leu  Phe  Gln  Glu  Tyr  Trp  Asp  Thr  Ile
1555                     1560                     1565

AGG  CCC  TTA  CTA  CAG  AGG  TGG  TGT  GGA  GAT  CCT  GCC  TTA  CTC  AAG  TCT                      4869
Arg  Pro  Leu  Leu  Gln  Arg  Trp  Cys  Gly  Asp  Pro  Ala  Leu  Leu  Lys  Ser
1570                     1575                     1580                          1585

TTG  AAG  CAG  AAA  AGT  GCT  GTG  GTC  AGG  TAC  CCT  AGA  AAA  AGA  AAT  AGT                      4917
Leu  Lys  Gln  Lys  Ser  Ala  Val  Val  Arg  Tyr  Pro  Arg  Lys  Arg  Asn  Ser
                    1590                     1595                     1600

TTG  ATA  GAG  CTT  CCT  GAG  GAC  TAC  AGC  TGT  CTT  CTA  AAT  CAG  GCT  TCT                      4965
Leu  Ile  Glu  Leu  Pro  Glu  Asp  Tyr  Ser  Cys  Leu  Leu  Asn  Gln  Ala  Ser
               1605                     1610                     1615

CAC  TTT  AGG  TGT  CCA  CGG  TCT  GCA  GAT  GAT  GAG  CGA  AAG  CAT  CCT  GTC                      5013
His  Phe  Arg  Cys  Pro  Arg  Ser  Ala  Asp  Asp  Glu  Arg  Lys  His  Pro  Val
          1620                     1625                     1630

CTC  TGT  CTT  TTC  TGT  GGG  GCC  ATC  CTG  TGT  TCT  CAG  AAC  ATC  TGT  TGC                      5061
Leu  Cys  Leu  Phe  Cys  Gly  Ala  Ile  Leu  Cys  Ser  Gln  Asn  Ile  Cys  Cys
1635                     1640                     1645

CAA  GAA  ATA  GTG  AAT  GGG  GAA  GAG  GTT  GGA  GCG  TGC  GTT  TTT  CAT  GCG                      5109
Gln  Glu  Ile  Val  Asn  Gly  Glu  Glu  Val  Gly  Ala  Cys  Val  Phe  His  Ala
1650                     1655                     1660                          1665

CTT  CAT  TGT  GGT  GCT  GGA  GTC  TGC  ATT  TTC  CTA  AAA  ATC  CGA  GAA  TGC                      5157
Leu  His  Cys  Gly  Ala  Gly  Val  Cys  Ile  Phe  Leu  Lys  Ile  Arg  Glu  Cys
               1670                     1675                     1680

AGG  GTG  GTC  CTG  GTG  GAA  GGA  AAA  GCC  AGA  GGC  TGT  GCC  TAC  CCA  GCC                      5205
Arg  Val  Val  Leu  Val  Glu  Gly  Lys  Ala  Arg  Gly  Cys  Ala  Tyr  Pro  Ala
          1685                     1690                     1695

CCT  TAC  TTG  GAT  GAA  TAT  GGA  GAA  ACA  GAC  CCA  GGG  CTA  AAG  AGA  GGA                      5253
Pro  Tyr  Leu  Asp  Glu  Tyr  Gly  Glu  Thr  Asp  Pro  Gly  Leu  Lys  Arg  Gly
                    1700                     1705                     1710

AAC  CCA  CTT  CAT  TTA  TCT  CGG  GAG  CGG  TAT  CGG  AAG  CTG  CAT  TTG  GTC                      5301
```

| | | | | | | | | | | | | | | | | |
|---|---|---|---|---|---|---|---|---|---|---|---|---|---|---|---|---|
| Asn | Pro | Leu | His | Leu | Ser | Arg | Glu | Arg | Tyr | Arg | Lys | Leu | His | Leu | Val | |
| | 1715 | | | | 1720 | | | | | 1725 | | | | | | |

| TGG | CAA | CAG | CAC | TGC | ATT | ATA | GAA | GAG | ATT | GCT | CGG | AGC | CAG | GAG | ACT | 5349 |
|---|---|---|---|---|---|---|---|---|---|---|---|---|---|---|---|---|
| Trp | Gln | Gln | His | Cys | Ile | Ile | Glu | Glu | Ile | Ala | Arg | Ser | Gln | Glu | Thr | |
| 1730 | | | | 1735 | | | | | 1740 | | | | | 1745 | | |

| AAT | CAG | ATG | CTA | TTT | GGA | TTT | AAC | TGG | CAG | TTA | CTC | TGAGCTTCAG | | | | 5395 |
|---|---|---|---|---|---|---|---|---|---|---|---|---|---|---|---|---|
| Asn | Gln | Met | Leu | Phe | Gly | Phe | Asn | Trp | Gln | Leu | Leu | | | | | |
| | | | 1750 | | | | | 1755 | | | | | | | | |

| | | | | | |
|---|---|---|---|---|---|
| TTCTGCCTCA | AGACAATCAT | GAGTGACATC | AATAATAAAG | ACTGATCTAA | AATTCTAGAG 5455 |
| AACTTTCTGA | GGACGGGGGA | AGTATTGGAG | GGTCTTTTGA | TCCATGTCCA | GATTCACACA 5515 |
| CATTAATAAA | ATATTCCTTA | ATGGAATATT | GCTTTCAATT | ATCAAACATA | AGCTTCAAGG 5575 |
| GAAAACAAG | ACATAGATTA | ATGTTTTATG | TTCTAGAACA | CTAAAGAAAT | GCTTGTTCAT 5635 |
| CCAAGTGTCT | ATTTCTGCTA | ATATTCCAG | AAAACTCCTT | TCCCTTCATA | ACTGTCCTAG 5695 |
| TTCATTTCAT | ATCACCCACC | TGGTTAATGA | GGTCACATTA | AGCATTTGTG | GACATTTCTC 5755 |
| CATCTGGCTA | ACATCTCTGC | ACCTTTGTAT | TTGGTGTTTC | TCGAGTGTAG | TTTAGCTTGG 5815 |
| GTTAGATCTC | TGAAAAGATG | CTGATCACCT | GTGATGGTCT | AAAGAGGAAT | TGCACAACTA 5875 |
| TGCAGTTTCT | TTCAATTAAA | AATTTCAAAA | CATGTAAACA | TCTTTCTTCT | TTAAGGAAAT 5935 |
| ATCCTTATTG | TACCACCTAC | GGCTTCAGTC | AGAAACAGAT | CTAAATCTCT | CTATGGAGAG 5995 |
| TGCTAGCTGT | GCTAGTCTGG | AAAGCATCCT | TCCAGTGTAG | ACCTCAAGTA | GATTCAGGAG 6055 |
| AATGTGCTCA | TTACGCATTC | CTTATACAAA | ATCCTGTTAT | CCTCACCTGA | TTCCAGGGAG 6115 |
| CTCTGTGGAG | TCACAAGTTC | TCCATCAGTT | ACATTCTTA | AGGCAGATTT | CTGCAGTAAG 6175 |
| ATCTCGTCTC | TTGGGGCCCC | ATCCTATTGT | CTCTCAGAAA | ACTCTTGTTT | TGAAGCAAAC 6235 |
| TCTTTGTAGA | ATGGGAATCA | GAAAATTGCC | CCAGTGAATG | GTCATAAGAG | ATGAAATTAG 6295 |
| AACACTGTAT | TTAAGCCAGT | TCTGCAACCT | TCTATGGCTT | GTAAGAAACA | GGTCCTTGAT 6355 |
| TTGATGTCTA | GGTGAAACCT | TTCATAAACG | ACTGTTTATG | | 6395 |

( 2 ) INFORMATION FOR SEQ ID NO:2:

( i ) SEQUENCE CHARACTERISTICS:
        ( A ) LENGTH: 1001 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..999

( x i ) SEQUENCE DESCRIPTION: SEQ ID NO:2:

| ATG | GAT | CCC | AAC | AAG | TTC | TTG | TTA | CTG | GTA | CTT | CAG | AGG | TAT | GAA | CTT | 48 |
|---|---|---|---|---|---|---|---|---|---|---|---|---|---|---|---|---|
| Met | Asp | Pro | Asn | Lys | Phe | Leu | Leu | Leu | Val | Leu | Gln | Arg | Tyr | Glu | Leu | |
| 1 | | | | 5 | | | | | 10 | | | | | 15 | | |

| GCC | GAG | GCT | TTT | AAC | AAG | ACC | ATA | TCT | ACA | AAA | GAC | CAG | GAT | TTG | ATT | 96 |
|---|---|---|---|---|---|---|---|---|---|---|---|---|---|---|---|---|
| Ala | Glu | Ala | Phe | Asn | Lys | Thr | Ile | Ser | Thr | Lys | Asp | Gln | Asp | Leu | Ile | |
| | | | 20 | | | | | 25 | | | | | 30 | | | |

| AAA | CAA | TAT | AAT | ACA | CTA | ATA | GAA | GAA | ATG | CTT | CAG | GTC | CTC | ATC | TAT | 144 |
|---|---|---|---|---|---|---|---|---|---|---|---|---|---|---|---|---|
| Lys | Gln | Tyr | Asn | Thr | Leu | Ile | Glu | Glu | Met | Leu | Gln | Val | Leu | Ile | Tyr | |
| | | 35 | | | | | 40 | | | | | 45 | | | | |

| ATT | GTG | GGT | GAG | CGT | TAT | GTA | CCT | GGA | GTG | GGA | AAT | GTG | ACC | AAA | GAA | 192 |
|---|---|---|---|---|---|---|---|---|---|---|---|---|---|---|---|---|
| Ile | Val | Gly | Glu | Arg | Tyr | Val | Pro | Gly | Val | Gly | Asn | Val | Thr | Lys | Glu | |
| | 50 | | | | | 55 | | | | | 60 | | | | | |

| GAG | GTC | ACA | ATG | AGA | GAA | ATC | ATT | CAC | TTG | CTT | TGC | ATT | GAA | CCC | ATG | 240 |
|---|---|---|---|---|---|---|---|---|---|---|---|---|---|---|---|---|
| Glu | Val | Thr | Met | Arg | Glu | Ile | Ile | His | Leu | Leu | Cys | Ile | Glu | Pro | Met | |

| | | | | | | | | | | | | | | | | |
|---|---|---|---|---|---|---|---|---|---|---|---|---|---|---|---|---|
| | | | | 65 | | | | | 70 | | | | | 75 | | 80 |
| CCA | CAC | AGT | GCC | ATT | GCC | AAA | AAT | TTA | CCT | GAG | AAT | GAA | AAT | AAT | GAA | 288 |
| Pro | His | Ser | Ala | Ile | Ala | Lys | Asn | Leu | Pro | Glu | Asn | Glu | Asn | Asn | Glu | |
| | | | | 85 | | | | | 90 | | | | | 95 | | |
| ACT | GGC | TTA | GAG | AAT | GTC | ATA | AAC | AAA | GTG | GCC | ACA | TTT | AAG | AAA | CCA | 336 |
| Thr | Gly | Leu | Glu | Asn | Val | Ile | Asn | Lys | Val | Ala | Thr | Phe | Lys | Lys | Pro | |
| | | | 100 | | | | | 105 | | | | | 110 | | | |
| GGT | GTA | TCA | GGC | CAT | GGA | GTT | TAT | GAA | CTA | AAA | GAT | GAA | TCA | CTG | AAA | 384 |
| Gly | Val | Ser | Gly | His | Gly | Val | Tyr | Glu | Leu | Lys | Asp | Glu | Ser | Leu | Lys | |
| | | 115 | | | | | 120 | | | | | 125 | | | | |
| GAC | TTC | AAT | ATG | TAC | TTT | TAT | CAT | TAC | TCC | AAA | ACC | CAG | CAT | AGC | AAG | 432 |
| Asp | Phe | Asn | Met | Tyr | Phe | Tyr | His | Tyr | Ser | Lys | Thr | Gln | His | Ser | Lys | |
| | | 130 | | | | | 135 | | | | | 140 | | | | |
| GCT | GAA | CAT | ATG | CAG | AAG | AAA | AGG | AGA | AAA | CAA | GAA | AAC | AAA | GAT | GAA | 480 |
| Ala | Glu | His | Met | Gln | Lys | Lys | Arg | Arg | Lys | Gln | Glu | Asn | Lys | Asp | Glu | |
| 145 | | | | | 150 | | | | | 155 | | | | | 160 | |
| GCA | TTG | CCG | CCA | CCA | CCA | CCT | CCT | GAA | TTC | TGC | CCT | GCT | TTC | AGC | AAA | 528 |
| Ala | Leu | Pro | Pro | Pro | Pro | Pro | Pro | Glu | Phe | Cys | Pro | Ala | Phe | Ser | Lys | |
| | | | | 165 | | | | | 170 | | | | | 175 | | |
| GTG | ATT | AAC | CTT | CTC | AAC | TGT | GAT | ATC | ATG | ATG | TAC | ATT | CTC | AGG | ACC | 576 |
| Val | Ile | Asn | Leu | Leu | Asn | Cys | Asp | Ile | Met | Met | Tyr | Ile | Leu | Arg | Thr | |
| | | | 180 | | | | | 185 | | | | | 190 | | | |
| GTA | TTT | GAG | CGG | GCA | ATA | AAC | ACA | GAT | TCT | AAC | TTG | TGG | ACC | GAA | GGG | 624 |
| Val | Phe | Glu | Arg | Ala | Ile | Asn | Thr | Asp | Ser | Asn | Leu | Trp | Thr | Glu | Gly | |
| | | 195 | | | | | 200 | | | | | 205 | | | | |
| ATG | CTC | CAA | ATG | GCT | TTT | CAT | ATT | CTG | GCA | TTG | GGT | TTA | CTA | GAA | GAG | 672 |
| Met | Leu | Gln | Met | Ala | Phe | His | Ile | Leu | Ala | Leu | Gly | Leu | Leu | Glu | Glu | |
| | 210 | | | | | 215 | | | | | 220 | | | | | |
| AAG | CAA | CAG | CTT | CAA | AAA | GCT | CCT | GAA | GAA | GAA | GTA | ACA | TTT | GAC | TTT | 720 |
| Lys | Gln | Gln | Leu | Gln | Lys | Ala | Pro | Glu | Glu | Glu | Val | Thr | Phe | Asp | Phe | |
| 225 | | | | | 230 | | | | | 235 | | | | | 240 | |
| TAT | CAT | AAG | GCT | TCA | AGA | TTG | GGA | AGT | TCA | GCC | ATG | AAT | ATA | CAA | ATG | 768 |
| Tyr | His | Lys | Ala | Ser | Arg | Leu | Gly | Ser | Ser | Ala | Met | Asn | Ile | Gln | Met | |
| | | | | 245 | | | | | 250 | | | | | 255 | | |
| CTT | TTG | GAA | AAA | CTC | AAA | GGA | ATT | CCC | CAG | TTA | GAA | GGC | CAG | AAG | GAC | 816 |
| Leu | Leu | Glu | Lys | Leu | Lys | Gly | Ile | Pro | Gln | Leu | Glu | Gly | Gln | Lys | Asp | |
| | | | 260 | | | | | 265 | | | | | 270 | | | |
| ATG | ATA | ACG | TGG | ATA | CTT | CAG | ATG | TTT | GAC | ACA | GTG | AAG | CGA | TTA | AGA | 864 |
| Met | Ile | Thr | Trp | Ile | Leu | Gln | Met | Phe | Asp | Thr | Val | Lys | Arg | Leu | Arg | |
| | | 275 | | | | | 280 | | | | | 285 | | | | |
| GAA | AAA | TCT | TGT | TTA | ATT | GTA | GCA | ACC | ACA | TCA | GGA | TCG | GAA | TCT | ATT | 912 |
| Glu | Lys | Ser | Cys | Leu | Ile | Val | Ala | Thr | Thr | Ser | Gly | Ser | Glu | Ser | Ile | |
| | 290 | | | | | 295 | | | | | 300 | | | | | |
| AAG | AAT | GAT | GAG | ATT | ACT | CAT | GAT | AAA | GAA | AAA | GCA | GAA | CGA | AAA | AGA | 960 |
| Lys | Asn | Asp | Glu | Ile | Thr | His | Asp | Lys | Glu | Lys | Ala | Glu | Arg | Lys | Arg | |
| 305 | | | | | 310 | | | | | 315 | | | | | 320 | |
| AAA | GCT | GAA | GCT | GCT | AGG | CTT | CAT | CGC | CAG | AAG | ATC | ATG | GC | | | 1001 |
| Lys | Ala | Glu | Ala | Ala | Arg | Leu | His | Arg | Gln | Lys | Ile | Met | | | | |
| | | | | 325 | | | | 330 | | | | | | | | |

NUCLEIC ACID ENCODING MAMMALIAN UBR1

BACKGROUND OF THE INVENTION

Features of proteins that confer metabolic instability are called degradation signals, or degrons (Varshavsky, Cell 64: 13–15 (1991)). The essential component of one degradation signal, termed the N-degron, is a destabilizing N-terminal residue of a protein (Bachmair, et al., Science 234: 179–186 (1986)). A set of N-degrons containing different destabilizing residues is referred to as the N-end rule, which relates the in vivo half-life of a protein to the identity of its N-terminal residue (for review see Varshavsky, Cell 69: 725–735 (1992) and Varshavsky, Cold Spring Harbor Symp. Quant. Biol. 60: 461–478 (1996)). The N-end rule pathway has been found in all species examined, including the eubacterium Escherichia coli, the yeast Saccharomyces cerevisiae, and mammalian cells. The N-end rules of these organisms are similar but distinct.

As discussed in greater detail below, ongoing studies have revealed that the N-end rule pathway participates in a variety of complex functions in eukaryotic systems. Such studies indicate that the ability to intervene at the molecular level to inhibit or modulate the N-end rule pathway offers an important therapeutic avenue. Given the relatively complex enzymology of the pathway, the availability of components in quantity is essential to the development of therapeutic methods.

SUMMARY OF THE INVENTION

The subject invention relates, on one aspect, to a nucleic acid sequence encoding a recognition component of the N-end rule pathway. This nucleic acid sequence is characterized by the ability to specifically hybridize to the nucleic acid sequence of SEQ ID NO 1 under stringent hybridization conditions. Such conditions are defined below. In another aspect, the invention relates to a nucleic acid sequence encoding a recognition component of the N-end rule pathway which is characterized by the ability to specifically hybridize to the nucleic acid sequence of SEQ ID NO 2 under stringent hybridization conditions. Other embodiments relate to DNA expression vectors containing nucleic acid sequences of the type described above, as well as cells transformed with such expression vectors. The invention also relates to applications for the compositions described above.

DETAILED DESCRIPTION OF THE INVENTION

Figure 1:
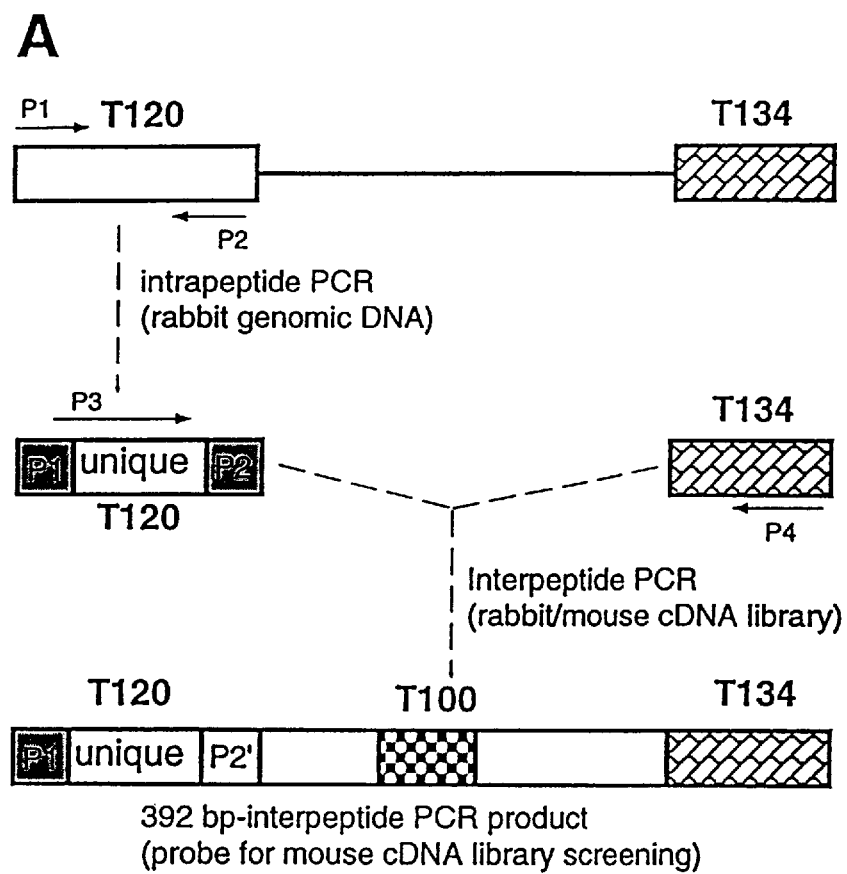
FIG. 1 is a diagrammatic representation of the strategy employed for the cloning of mouse Ubr1 cDNA by intrapeptide PCR, interpeptide PCR, followed by conventional library screening.

The present invention is based on the isolation and cloning of nucleic acids encoding both human and murine forms of the recognition component of the N-end rule pathway, Ubr1. Ubr1, also referred to as E3α, is a ubiquitin-protein ligase which has been linked, in particular, to stress-related deterioration (wasting) of muscle tissue.

More specifically, the rapid loss of muscle proteins associated with a variety of disease states has been shown to be primarily due to enhanced proteolysis via the ubiquitin-proteasome pathway (Mitch and Goldberg, N. Eng. J. Med. 335: 1897 (1996)). In rabbit skeletal muscle extracts, the N-end rule pathway is the dominant pathway for protein degradation—catalyzing the complete degradation of soluble proteins to amino acids (Solomon et al., J. Biol. Chem. 271: 26690 (1996)). In soluble extracts of rabbit muscle tissue, known inhibitors of the Ubr1 gene product were demonstrated to reduce the ATP-dependent degradation of soluble muscle proteins to amino acids by blocking their conjugation to $^{125}$I-ubiquitin (Solomon et al., Abstracts from 1997 FASEB Summer Meeting, Vermont (1997)).

Solomon et al. (Abstracts from 1997 FASEB Summer Meeting, Vermont (1997)) also report the identification of changes in the rate of protein ubiquitination associated with a number of pathological states characterized by muscle proteolysis. More specifically, in atrophying rat muscles, when overall protein degradation increases (e.g., in septic rats with sepsis induced by cecal puncture), hyperthyroid rats (treated with triiodothyronine) or in tumor-bearing rats (carrying Yoshida Ascites Hepatome for 3 to 5 days)), $^{125}$I-ubiquitin conjugation to soluble proteins increased 2-fold above the levels found in control muscles. Introduction of a known inhibitor was found to selectively suppress the increased $^{125}$I-ubiquitin conjugation toward levels in control muscles. In addition, ubiquitination of $^{125}$I-lysozyme (a model N-end rule substrate) was also determined to increase by 2-fold in extracts of atrophying muscles above levels in control extracts. Following hypophysectomy or thyroidectomy, protein degradation was shown to fall in isolated rat muscles. In extracts of such muscles, $^{125}$-I-ubiquitin conjugation to soluble proteins also falls by 50% in parallel with protein degradation. Addition of the lysine-alanine dipeptide suppressed $^{125}$I-ubiquitin conjugation to soluble proteins and eliminated most of the differences in this process between control and hypophysectomized or thyroidectomized rat muscle extracts. Ubiquitination of $^{125}$I-lysozyme was also reduced in these extracts indicating that the activities of components of the N-end rule pathway fall in muscles of thyroidectomized and hypophysectomized rats.

Observations such as those set forth above suggest that inhibitors of the N-end rule pathway will prove useful in connection with the treatment of various diseases characterized by the wasting of muscle tissue. While certain inhibitors of the N-end rule pathway are known (e.g., dipeptides resembling substrates of the N-end rule) the in vivo utility of such inhibitors is limited. Thus, one aspect the present invention relates to methods and compositions for inhibiting the N-end rule pathway-mediated muscle deterioration.

In addition to the treatment of various diseases characterized by the wasting of muscle tissue, the inhibition of the N-end rule pathway is indicated as a means of intervention for treatment of infection by intracellular pathogens such as Lysteria monocytogenes and Yersinia enterocolitica. Intracellular pathogens of this type occupy the cytoplasm of an infected cell, and propagate without killing the cell. An organism attempts to rid itself of infection by such pathogens through degradation of the pathogen's constituent proteins intracellularly, followed by the presentation of bacterial protein fragments to the immune system of the host via the major histocompatibility complex (MHC) class I-associated cytolytic T lymphocyte epitopes.

A recent report by Sijts et al. (J. Biol. Chem. 272: 19261 (1997)) highlights the involvement of the N-end rule pathway in connection with the MHC-associated presentation of Listeria monocytogenes epitopes. More specifically, the investigators focused on the degradation of p60, a Listeriasecreted murein hydrolase. Roughly 3% of degraded p60 gives rise to p60 217–225, a nonamer peptide that is bound by H-2K$^d$ MHC class I molecules. Mutagenesis of the N-terminal residue of p60 to replace the wild-type residue with amino acids known to be either stabilizing or destabilizing according to the N-end rule demonstrated clearly that p60 is a substrate of the N-end rule pathway. Valine substitution dramatically stabilized cytosolic p60 molecules, whereas aspartic acid substitution resulted in rapid degradation.

Cytosolic antigen degradation is fundamental to the generation of most MHC class I presented peptides. The fact that such degradation is, in the case of intracellular pathogens, mediated by the N-end rule pathway, strongly suggests intervention and manipulation of the pathway can be used to treat such infections. While the definitive demonstration of the importance of the N-end rule pathway in the life cycle of an invading bacterium such as *L. monocytogenes* remains to be demonstrated directly, the basis for the comments relating to therapy is the fact that intracytosolic parasites such as *L. monocytogenes* co-evolved with the N-end rule pathway. Therefore, drug-mediated perturbations of this pathway (either its inhibition or activation) are extremely likely to influence the course of infection by these bacteria.

Discussed above are examples of two pathological states, stress-induced deterioration of muscle tissue and infection by an intracellular pathogen, which are amenable to treatment by molecular intervention involving the N-end rule pathway. The N-end rule pathway has been well-studied and is the subject of several comprehensive review articles (see e.g., Varshavsky, *Trends Biochem. Sci.* 22: 383 (1997) and Varshavsky, *Proc. Natl. Acad. Sci. USA* 93: 12142 (1996)).

A brief review of the enzymology of the N-end rule pathway is warranted. Eukaryotic cells contain ubiquitin-specific enzymes that catalyze reactions whose product is either a single ubiquitin moiety or a multi-ubiquitin chain covalently linked to an acceptor protein. Ubiquitin is conjugated to other proteins through an amide bond, called the isopeptide bond, between the C-terminal (Gly-76) residue of ubiquitin and the $\epsilon$-amino group of a lysine residue in an acceptor protein.

Ubiquitin is activated for conjugation to other proteins by a ubiquitin-activating enzyme (E1), which couples ATP hydrolysis to the formation of a high-energy thioester bond between Gly-76 of ubiquitin and a specific cysteine residue of E1. The E1-linked ubiquitin moiety is moved, in a transesterification reaction, from E1 to a cysteine residue of a ubiquitin-conjugating enzyme (E2), and from there to a lysine residue of an ultimate acceptor protein, yielding a ubiquitin-protein conjugate. This last step requires the participation of another component, called E3 or recognin, which selects a protein for ubiquitylation through an interaction with its degradation signal. Ubr1p, the E3 of the N-end rule pathway, is a bona fide enzyme that acts at the step between an E2 and an ultimate acceptor of ubiquitin. It catalyzes the movement, through transesterification, of the ubiquitin moiety from the cysteine residue of a relevant E2 enzyme to a cysteine residue of E3 itself.

Ultimately, ubiquitin-protein conjugates generated by the cascade of enzyme-catalyzed reactions described above, are specifically degraded by an approximately 2,000 kDa, ATP-dependent protease, termed the 26S proteasome. The 26S proteasome consists of a 20S core proteasome and a complex containing multiple ATPases at both ends of the 20S proteasome.

Ubr1 is one of several E3-type proteins of the ubiquitin system. Ubr1 is specific, in particular, for "destabilizing" residues exposed at the N-terminus of protein substrates. Since the degradation signals recognized by Ubr1 represent only a relatively small subset of the signals recognized by the entire ubiquitin system, inhibition of Ubr1 (and hence inhibition of the N-end rule pathway) would be a relatively mild, non-lethal therapeutic intervention, whereas the inhibition of the entire ubiquitin system would be lethal in mammalian cells, and therefore undesirable for selective therapy.

Inhibition of the Ubr1-encoded function in a cell can be effected in a variety ways. For example, at the nucleic acid level, an inhibitory molecule which specifically hybridizes to the Ubr1 mRNA can be contacted with the Ubr1 mRNA under physiological conditions, thereby inhibiting translation of the Ubr1 mRNA. Alternatively, inhibitors of the translated Ubr1 gene product can be introduced. With respect to inhibition at the translation level, knowledge of the Ubr1 cDNA sequence is essential. With respect to inhibition of the translated Ubr1 gene product, the availability of a cloned nucleic acid sequence encoding Ubr1 is a virtual necessity, for example, for the production of quantities of Ubr1 necessary for screening assays.

Thus, in one aspect, the present invention relates to a nucleic acid sequence encoding the Ubr1 recognition component of the N-end rule pathway. Disclosed herein are cDNA sequences corresponding to murine and human forms of Ubr1.

Given the nucleic acid sequences provided herein, one of skill in the art using no more than routine experimentation could isolate full length cDNAs from virtually any mammalian source. These cDNAs could be inserted into eukaryotic or prokaryotic expression vectors for the production of Ubr1 using recombinant DNA techniques. The scope of Applicants' invention is not limited to the specifically disclosed sequences, but rather encompass variations of such sequences which: 1) hybridize to the disclosed sequences under stringent hybridization conditions; and 2) encode a functional Ubr1 protein. With respect to the first criteria, an example of stringent hybridization conditions includes hybridization in which the disclosed sequences (or a portion thereof) are fixed to a solid support and a second DNA molecule to be tested for the ability to hybridize to the disclosed sequences is detectably labeled and suspended in a hybridization buffer consisting essentially of 50% formamide, 5×SSPE (1×SSPE is 0.15 mM NaCl, 1 mM Na-EDTA, 10 mM Na-phosphate (pH 7.0), 5×Denhardt's solution (0.1% polyvinylpyrrolidone, 0.1% Ficoll)). The hybridization buffer is contacted with the solid support at a temperature of about 45° C. for a period of several hours. The hybridization solution is then removed, and non-specifically bound nucleic acid is removed by repeated washing with 1×SSC at increasing temperatures (up to 65° C.). With respect to the second criteria, the functionality of an encoded product can be determined by a variety of assay techniques including, for example, any of the in vitro techniques discussed below.

Inhibition of Ubr1 mRNA translation may be effected by introducing oligonucleotides, or oligonucleotide combinations into a cell of interest. Alternatively, an antisense gene construct encoding a transcription product which is complementary with at least a portion of the Ubr1 mRNA may be employed. Due to the inherent difficulties associated with the introduction of oligonucleotides into the cells of an organisms, the use of an antisense gene construct is preferred in a therapeutic context. An antisense gene construct may be produced, for example, by inserting at least a portion of double-stranded Ubr1 cDNA into an expression vector in reverse orientation, as compared to the wild-type context, relative to a promoter. The expression vector is selected to be suitable for use in the target cell type. For use in connection with therapy in humans, eukaryotic virus-based vectors are preferred. Preferably, the nucleic acid encoded by the reverse gene construct is complementary with the Ubr1 mRNA in a region known to be critical with respect to expression. Typically, initial designs include translation start sites, splice junctions, and other sites critical with respect to expression.

As an alternative to the inhibition of translation of the Ubr1 mRNA, strategies designed to inhibit the activity of the translated Ubr1 gene product are employed. For example, contacting the expressed Ubr1 gene product with a molecule which specifically binds to the Ubr1 gene product and inhibits its activity is a preferred method of inhibition.

A variety of methods may be employed to identify a specific inhibitor of the Ubr1 gene product. For example, using a DNA expression vector containing expressible Ubr1 cDNA, the Ubr1 gene product may be overexpressed in vitro. The in vitro system is supplemented with the relevant ubiquitin conjugating enzyme (E2), the mammalian ubiquitin activating enzyme (E1), free ubiquitin and ATP in amounts sufficient to support ubiquitylation of substrates of the N-end rule pathway. Once established, this in vitro system is employed to screen small molecule libraries for the identification of inhibitors which exert their effect in an ATP and Ubr1-dependent manner. Such small molecule libraries are assembled from sources rich in complex small organic molecules. Bacterial and plant cell extracts are frequently used sources for the isolation of a large number of diverse organic molecules for such screening purposes.

Another method suitable for the identification of a specific inhibitor of the Ubr1 gene product involves the overexpression of the Ubr1 gene product in a mammalian cell line. Again, an expression vector is carefully selected to be compatible with the preferred mammalian cell line. In preferred embodiments, the cell line employed is a human cell line. The overexpression of the Ubr1 gene product in the mammalian cell line would increase the activity of the N-end rule pathway in the cell culture. In such a Ubr1-enhanced assay, inhibitors are detectable at a far greater level of sensitivity than would otherwise be provided by a wild-type cell line.

The availability of the Ubr1 cDNA sequence also provides the opportunity for the identification of specific inhibitors by a rational approach based on a complete understanding of the Ubr1 atomic architecture. The availability of the Ubr1 cDNA enables the production of the Ubr1 gene product by recombinant DNA techniques in milligram quantities. The recombinantly produced Ubri gene product can be crystallized, and its structure determined at atomic resolution by X-ray diffraction techniques. Using such techniques in combination with conventional molecular modelling, rationally designed candidate inhibitor molecules, designed to interact with specific subdomains of the Ubr1 gene product are designed and tested.

EXEMPLIFICATION

Materials and Methods i) peptide preparation and sequencing

Rabbit Ubr1 protein (previously termed E3α) was purified from reticulocyte lysate using immobilized-protein column and elution by dipeptides as described (Reiss and Hershko, *J. Biol. Chem* 265: 3685–3690 (1990)). The sample containing approximately 20 μg (~100 pmol) of the purified Ubr1 protein and chicken ovalbumin as a stabilizer for Ubr1 activity, in 50 mM N-ethyl morpholine, pH 8.5, 0.2 mM $CaCl_2$ and 10% isopropanol, was digested with trypsin at an enzyme-substrate mass ratio of 1:20 at ambient temperature for 24 hrs. The digested sample was dried and resuspended in 6M guanidine-HCl, 0.1% trifluoroacetic acid (TFA). The tryptic peptides were fractionated by reverse-phase HPLC on a C18 column and eluted with a gradient of acetonitrile in 0.1% TFA. The isolated peptides were sequenced by automated Edman degradation on a model 470A/900/120A gas phase sequencer/on-line analyzer (Applied Biosystems) using standard chemistry. Fourteen sequences of different peptides were obtained.

ii) Intrapeptide and interpeptide PCR.

Based on the rabbit Ubr1 peptide sequences, the intrapeptide PCR with degenerate oligonucleotides using rabbit genomic DNA (Clontech) as a template was applied to amplify the unique rabbit Ubr1 cDNA sequence corresponding to the internal region of the two PCRs (FIG. 1). Specifically, immediately prior to initiation of the PCR reaction, PCR primers were boiled for 1 min. and immediately cooled on ice. The PCR premixtures (100 μl reaction volume) without AmpliTaq DNA polymerase were preincubated at 72° C. (3 min.) in GeneAmp PCR System 9600 (Perkin-Elmer) and then AmpliTaq polymerase was added to each tube containing the premixture. After 94° C. for 2 min., the first 4 cycles were done at 94° C. for 1 min., 65° C. for 10 min., and 72° C. for 1 min. In the following 20 cycles, the factors in PCR were gradually decreased every four cycles; the denaturation time to 50, 30, 25, 20, and 15 sec; the annealing temperature to 62, 58, 55, 50, and 45° C.; the annealing time to 5, 4, 3, 3, and 2 min.; and the extension time to 50, 30, 25, 25, and 25 sec. Then the final 20 cycles were done at 94° C. for 15 sec, 42° C. for 2 min., and 72° C. for 25 sec. The amplified intrapeptide PCR products were analyzed by electrophoresis in a 4% low melting temperature agarose gel, cloned into PCR2.1 vector (Invitrogen, Calif.) and screened by digestion with restriction enzymes and subsequent sequencing.

Three PCRs gave the intrapeptide PCR products which contained the expected deduced amino acid sequences. The PCR primer pairs used for the positive clones were designated as follows: T122 (forward and reverse); T120 (forward and reverse); and T96 (forward and reverse). These designations correspond to the designations assigned to 3 of the 14 rabbit peptide sequences determined as described above.

Subsequently, the oligonucleotides corresponding the unique sequence of the intrapeptide PCR products using rabbit liver cDNA library (Clontech) as a template were applied to get Ubr1 cDNA fragment between the two peptides (interpeptide PCR) (FIG. 1). Among many combinations of primers, an oligonucleotide containing the unique sequence of T120 and another degenerate oligonucleotide corresponding to T134 (another of the 14 rabbit peptide sequences determined) produced a 392 bp fragment. Subsequently, the 392 bp-mouse Ubr1 cDNA fragment corresponding to the 392 bp-rabbit Ubr1 cDNA fragment was obtained from the mouse cDNA library (Clontech) using an oligonucleotide containing the unique intrapeptide PCR of mouse T120 and a degenerate oligonucleotide corresponding to rabbit T134. The 392 bp-mouse Ubr1 cDNA fragment was used as a probe for the screening of the Ubr1 cDNA clone from the mouse cDNA library as described below.

iii) cDNA Library Screening, DNA Sequencing, and 5'- and 3'-RACEs.

The λgt11 liver cDNA library (Clontech) was plated on *Escherichia coli* Y1090 (about $3\times10^4$ plaque-forming units/150-mm plate, total 30 plates), and the plaques were lifted onto nylon membrane (Hybond-N, Amersham) and screened by hybridization with the 392 bp-mouse cDNA fragment (obtained from interpeptide PCR) that was labeled with [$^{32}$P]dCTP. The putative positive clones were rescreened until they were plaque-purified. This initial screening using a λgt11 liver cDNA library gave two positive plaques. The purified DNA was digested with EcoRI and then analyzed on 1% agarose gels. Both of the selected positive clones turned out to contain identical 2.45 kb insert by the partial sequencing of the eluted PCR products produced with λDNA and 392 bp-probe specific primers. The cDNA inserts of the two clones were then subcloned into the pBluescript II SK$^+$ plasmid vector, one of them (MR3) was sequenced on both strands. The complete sequencing of MR3 revealed nine regions in deduced amino acid sequence, including the regions of the 392 bp-mouse probe corresponding to T120, T100 and T134, which showed strong identity (62%–100%) to that of the rabbit peptide sequences. The overall identity and similarity of the sum of the nine regions (196 aa) to those of rabbit peptide sequences were 89% and 90%, respectively. This fact indicates that the cloned 2.45 kb insert encodes the mouse homolog of rabbit Ubr1. Furthermore, although the overall homology is relatively low (24% identity and 50% similarity), the deduced amino acid sequence (812 aa from N-terminus) of the cloned 2.45 kb insert showed considerable homology to that (aa 3–960) of *S. cerevisiae* UBR1, further supporting that the cloned 2.45 kb insert encodes the mouse homolog of *S. cerevisiae* UBR1.

The region of similarity began from the ATG codon located between nt 12 and 14 in 2.45 kb sequence, suggesting that this ATG codon may be the start codon in the mouse Ubr1 ORF. There was no stop codon, the poly(A) addition signal or poly(A) tail downstream of the ATG codon, suggesting that the cloned 2.45 kb insert encodes partial N-terminal portion of the mouse Ubr1 ORF considering the observed molecular weight of the purified rabbit Ubr1 (~180 kDa) on SDS-polyacrylamide gel electrophoresis (Reiss and Hershko, *J. Biol. Chem* 265: 3685–3690 (1990)), which is slightly smaller than *S. cerevisiae* UBR1 (225 kDa). Since there was no inframe stop codon upstream of the ATG codon, 5'-RACE PCR (Frohman et al., *Proc. Natl. Acad. Sci. USA* 85: 8998–9002 (1988)) was employed to amplify the upstream region, which contains the inframe stop codon, using an oligonucleotide primer specific for the 2.45 kb clone and a primer complementary to an in vitro-produced 5'oligo(dA) tract.

Specifically, 500 ng of poly(A)$^{30}$ RNA, isolated from mouse L-cells using Oligotex Direct mRNA kit (QIAGEN), was mixed with diethylpyrocarbonate-treated water to make the final volume of 20 μl, incubated at 70° C. for 5 min., and cooled on ice. To this sample were added 20 pmols of a primer corresponding to the antisense strand of the mouse Ubr1 ORF (nt 313–338 in SEQ ID NO:1), 2 μl of 10× PCR buffer (Perkin-Elmer), 2 μl of 0.1M dithiothreitol (DTT), 1 μl of 10 mM dNTPs, 1 μl of 25 mM MgCl$_2$, and 1 μl of bovine serum albumin (BSA; 2 mg/ml). The sample was incubated at 42° C. for 2 min., followed by the addition of 1 μl of Superscript II reverse transcriptase (Gibco-BRL) and an incubation at 42° C. for another 40 min. The temperature was increased to 55° C., followed by the addition of 1 μl of RNAase H (Gibco-BRL; 2 units/μl) and incubation for 20 min. The resulting cDNA products were purified with QIAquick PCR purification kit (QIAGEN), and were eluted with 50 μl of water. To produce a cDNA-linked 5'oligo(dA) extension, 5 μl of purified cDNA was diluted with 11.5 μl of water, incubated at 70° C. for 5 min., cooled on ice, then mixed with 1 μl of 10× PCR buffer (to the final concentration of 0.5×), 1 μl of 25 mM MgCl$_2$, 0.5 μl of BSA (2 mg/ml), 0.5 μl of 10 mM dCTP, and 0.25 μl of terminal transferase (Boehringer Mannheim). After an incubation at 37° C. for 5 min., the enzyme was inactivated by heating the sample at 65° C. for 10 min. The first round of RACE-PCR amplification was carried out in a 100 μl sample containing 10 μl of 10× PCR buffer, 2.5 mM MgCl$_2$, 5 μl of cDNA linked to oligo(dC), 20 pmols of a primer corresponding to the antisense strand of Ubr1 ORF (nt 306–332 in SEQ ID NO:1), and 20 pmoles of oligo(dA) anchor primer. The sample was incubated at 94° C. for 5 min., then at 57° C. for 8 min., followed by the addition of AmpliTaq DNA polymerase (Perkin-Elmer) and incubation at 72° C. for 8 min. to produce the complementary cDNA strand. Thereafter, 35 cycles of a 3-step PCR amplification were carried out. Each step involved consecutive incubations for 30 sec at 94° C., 1 min. at 57° C., and 2 min. at 72° C. 2 μl of the first-round PCR product was used for the second-round PCR that utilized, in the same total volume, 0.4 nmols of T-adapter primer (same as the T-anchor primer but lacking T$_{17}$), and 0.4 nmols of a primer corresponding to the antisense strand of Ubr1 ORF (nt 271–293 in SEQ ID NO:1). The PCR-produced DNA fragments were inserted into pCR2.1 vector (Invitrogen). Two of the resulting clones gave the 114 bp-upstream sequence of the ATG codon, which contains two successive in-frame stop codons 48 bp and 93 bp upstream of the above ATG codon, suggesting that the putative Met start codon is the likely in vivo start codon of Ubr1 ORF.

Since several lines of evidences (see above and Results) indicated that the cloned 2.45 kb insert encodes partial N-terminal portion of the mouse Ubr1 ORF and since another hybridization screening of the same filters with the cloned 2.45 kb insert as a probe gave no additional positive clones, we employed 3'-RACE to amplify the downstream region of the 2.45 kb insert to use it as a probe for the next cDNA library screening. The 3'-RACE, which was done similarly to 5'-RACE (above) except omitting homopolymer tailing in 3'-RACE, gave 1.3 kb product (corresponding nt 1985–3313 in SEQ ID NO:1) which overlapped with 2.45 kb sequence by 465 bp. Based on the sequence of the 1.3 kb 3'-RACE product, one more 3'-RACE was done and gave 1.2 kb (corresponding nt 3039–3835 in mouse Ubr1 cDNA sequence), in which 797 bp Ubr1 cDNA sequence was fused with the 3'-UTR region of mouse glutathione S-transferase (GST) mRNA, which seems to be an artifact.

To get full length cDNA, λgt10 cDNA library (Clontech) from MEL-C19 cells was plated on *Escherichia coli* C600Hfl, hybridized with a labeled 998 bp-probe (nt 2470–3467 SEQ ID NO:1) synthesized by PCR on the basis of the sequence from 3'-RACE. By PCR analysis of the positive plaque lysates (or phage λDNA) followed by partial sequencing, the insert size and relative location of each of fourteen independent positive clones ranging in size from 0.6 to 4.6 kb were determined. Among them, five clones which overlap each other and cover the full length cDNA were subcloned into Bluescript II SK$^+$ (MR16 with size of 3.0 kb, MR17 with size of 2.8 kb, MR19 with size of 2.2 kb, MR20 with size of 1.4 kb, and MR23 with size of 4.6 kb) and sequenced on both strands. Especially in the ORF region, at least two independent clones (from cDNA library screening, 5'- or 3'-RACE) were sequenced. Among them, MR16 contained the putative ATG start codon of the initial clone (2.45 kb, see above) preceded by 57 bp-mouse Ubr1

5'-UTR containing an inframe stop codon 48 bp upstream of the ATG codon. The 57 bp-5'-UTR region of MR16 was preceded by 360 bp mouse 18S ribosomal RNA sequence (EMBL accession number X00686), which is thought to be an artifact during library construction. MR19 contained an ORF showing considerable homology to yeast UBR1 followed by a stop codon preceding a poly(A) addition signal 41 bp downstream which was followed by poly($A_{21}$) tail 9 bp downstream, suggesting that MR19 contains Ubr1 C-terminal region and 3'-UTR. MR20 overlapped with 3'-region of MR16 and 5'-region of MR19, suggesting that MR16, MR20 and MR19 covers the full length ORF of mouse Ubr1 cDNA and also 3'- and 5'-UTR regions. These three clones (MR16, MR20 and MR19) were joined into a single contiguous fragment to make MR26 which contains 57 bp-5'UTR, 5271 bp Ubr1 ORF (1757 residues) and 58 bp-3'-UTR. Specifically, the 1.2 kb-EcoRI-XbaI fragment of MR20 was subcloned into pBluescript II SK$^+$ to yield MR24. Subsequently, the 2.2 kb-XbaI fragment of MR19 was subcloned into MR24 to make MR25. Then the 3 kb-MscI-NotI fragment of MR25 was inserted into MR16 to make MR26 which contains the full length mouse Ubr1 ORF shown in SEQ ID NO:1.

iv) Cloning of Partial Human UBR1 cDNA fragment (1 kb) using RT-PCR

Poly(A)$^+$ RNA was isolated from human 293 cells using Oligotex Direct mRNA kit (QIAGEN). The first-strand cDNA was synthesized from 500 ng of Poly(A)$^+$ RNA using oligo(dT) priming and Superscript II reverse transcriptase (Gibco-BRL), followed by treatment of 2 units of RNAase H (Gibco-BRL) and purified with QIAquick PCR purification kit (QIAGEN). 30 ng of the synthesized cDNA was used for PCR using AmpliTaq DNA polymerase (Perkin-Elmer) and several different primers sets corresponding to mouse Ubr1 cDNA sequence. One of the reactions gave the 1 kb product which was subcloned into pCR2.1 vector (Invitrogen) and sequenced. The sequence of the partial human UBR1 cDNA fragment is shown in SEQ ID NO:2.

v) Cloning of Partial Human UBR1 Genomic DNA Fragments using Genomic PCR

The human genomic DNA was isolated from human 293 cells by conventional method and was used for PCR using Expand High Fidelity PCR System (Boehringer Mannheim) and exon specific primers. The PCR products were subcloned into pCR2.1 vector (Invitrogen) to give HR8 (insert size 6.3 kb), HR6-4 (insert size 5.8 kb), HR2-25 (insert size 3.6 kb), HR7-2 (insert size 5.4 kb). The four inserts described above were analyzed by partial DNA sequencing and were shown to cover ~21 kb of the human UBR1 gene with overlapping of 100–150 bp. The exon/intron junctions were determined by partial sequencing.

vi) Northern and Southern Hybridizations

Mouse and human multiple tissue Northern blots with 2 μg of poly(A)$^+$ RNA per lane (Clontech), isolated from various adult mouse or human tissues, were hybridized with the $P^{32}$-labeled probes (1 kb-human UBR1 cDNA fragment for human blot and 2 kb and 648 bp mouse Ubr1 CDNA fragments corresponding to nt 116–2124 and nt 4738–5385, respectively, in mouse Ubr1 cDNA sequence (SEQ ID NO: 1) eluted from the gel after PCR. Hybridization was carried out as suggested in the manufacturer's protocol. The intactness of the RNA samples on the blots were checked with the β-actin probe provided with them. For Southern blot analysis genomic DNAs, isolated by conventional method from mouse L-cell and human 293 cell and digested with various restriction enzymes, were hybridized with 1228 bp or 1169 bp mouse Ubr1 cDNA probes for mouse blot (corresponding to nt 105–1332 and nt 610–1778, of SEQ ID NO: 1, respectively) or 1 kb human UBR1 CDNA probes for human blot under either high stringency (final washing; 0.1× SSC/ 0.1% SDS at 55° C.) or low stringency conditions (final washing; 0.2× SSC/0.1% SDS at 42° C.).

vii) Interspecific Mouse Backcross Mapping

The chromosomal position of mouse Ubr1 was determined using the interspecific backcross analysis. Interspecific backcross progeny were generated by mating (C57BL/ 6J×M. spretus) $F_1$ females and C57BL/6J males as described (Copeland and Jenkins, Trends Genet. 7: 113–118 (1991)). A total of 205 $N_2$ mice were used to map the Ubr1 locus (see text for details). DNA isolation, restriction enzyme digestion, agarose gel electrophoresis, Southern blot transfer and hybridization were performed essentially as described (Jenkins et al., J. Virol. 43: 26–36 (1982)). All blots were prepared with Hybond-N$^+$ nylon membrane (Amersham). A 1169 bp-fragment of mouse cDNA corresponding to nt 610–1778, was labeled with [$\alpha^{32}$P] dCTP using a random primed labeling kit (Stratagene); washing was done to a final stringency of 1.0×SSC, 0.1% SDS, 65° C. Fragments of 5.6, 5.4, and 4.3 kb were detected in ScaI digested C57BL/6J DNA and a fragment of 15.0 kb was detected in ScaI digested M. spretus DNA. The presence or absence of the 15.0 kb ScaI M. spretus-specific fragment was followed in backcross mice. A description of the probes and RFLPs for the loci linked to Ubr1 including Thbs1 and B2m has been reported previously (Lawler et al., Genomics 11: 587–600 (1991)). One locus has not been reported previously for this interspecific backcross. The probe for erythrocyte protein band 4.2 (Epb4.2) was an ~800 bp EcoRI fragment of human cDNA that detected a 7.8 kb SphI fragment in C57BL/6J DNA and a 14.0 kb SphI fragment in M. spretus DNA. Recombination distances were calculated using Map Manager, version 2.6.5. Gene order was determined by minimizing the number of recombination events required to explain the allele distribution patterns.

vii) Human chromosome mapping. Fluorescence in situ hybridization (FISH) was performed on human chromosomes prepared from synchronized cultures of lymphocytes isolated from cord blood (Heng et al, Proc. Natl. Acad. Sci. USA 89: 9509–9513 (1992)). Human chromosomes were probed with mixture of plasmids (HR8, HR6-4, HR2-25, and HR7-2) containing human UBR1 genomic DNA fragments (~21 kb) corresponding to partial human UBR1 cDNA fragment (1 kb, nt 2540–3532 in SEQ ID NO: 1). Probes were labeled with biotinylated DATP using the BRL BioNick labeling kit (15° C., 1 hr), hybridized to the chromosome spreads, and detected with FITC-avidin. Signals were amplified by incubation with biotinylated goat anti-avidin followed by a second round of incubation with FITC-avidin. Chromosome banding patterns were obtained with the chromatin-binding fluorescent dye 4'-6-diamino-2-phenylindole (DAPI). Chromosomal localization of human UBR1 was made by superimposing photographs of the hybridization signals with photographs of the DAPI banding patterns.

Results i) Peptide sequencing and PCR cloning

The fourteen peptide sequences of the purified rabbit Ubr1 protein showed no significant homology to any of the proteins deposited in the database, even to S. cerevisiae UBR1 protein, a counterpart of rabbit Ubr1 protein. A second independent purification of rabbit Ubr1 protein from reticulocyte lysates using similar method with that of the first approach (Reiss and Hershko, J. Biol. Chem 265: 3685–3690 (1990)) followed by determination of tryptic peptide sequences was done and gave three peptide sequences (PEP1, PEP2 and PEP3) which are identical to those of the first approach, supporting that the purified protein and the determined sequences are authentic.

On the basis of the peptide sequences, an initial attempt was made to obtain the unique sequence (not degenerate) of rabbit Ubr1 cDNA using degenerate oligonucleotide primers and intrapeptide PCR, which amplify the internal region of a peptide sequence (FIG. 1 and see *Materials and Methods*). Unique sequences were determined from intrapeptide PCR and corresponded to regions of sequence encoding several of the 14 rabbit peptide sequences (e.g., T122, T120 and PEP2). The intrapeptide PCR of T120 from mouse λgt11 liver cDNA gave a unique sequence encoding the same amino acids (with third codon redundancies) with that from rabbit genomic DNA of T120. The unique sequence of PEP1 was variable (four different types in 8 clones). The reason for this variable unique sequences is unclear. Subsequently, the oligonucleotide PCR primers, bearing the unique sequence from intrapeptide PCR, together with the original degenerate PCR primers were used for the amplification of rabbit Ubr1 cDNA fragment between the peptide sequences from rabbit liver cDNA library (interpeptide PCR) (FIG. 1). One of the interpeptide PCRs yielded a 392 bp-PCR product bearing T120 and T134 on both ends, and also internally bearing T100, indicating it to be authentic rabbit Ubr1 cDNA fragment corresponding to the purified protein. A 392 bp-mouse Ubr1 cDNA fragment corresponding to the 392 bp-rabbit UBR1 cDNA fragment was also obtained from the mouse cDNA library (see *Materials and Methods*). Sequencing of the 392 bp-mouse Ubr1 cDNA fragment revealed three regions corresponding to T120, T100 and T134 peptide sequences of 392 bp-rabbit Ubr1 cDNA fragment. The 392 bp-rabbit and mouse Ubr1 cDNA fragments shared 88% and 89% identity in nucleotide and protein sequence, respectively. They showed no significant homology to any sequence in data base including *S. cerevisiae* UBR1.

ii) Isolation of mouse Ubr1 cDNA

In the initial cDNA screening using the 392 bp-mouse cDNA fragment and subsequent screening using a probe based on the 3-RACEs gave several positive clones ranging in size from 0.6 to 4.6 kb. Among them, MR16 with size of 3.0 kb containing the ATG start codon preceded by 57 bp-5'-UTR with an in-frame stop codon 48 bp upstream of the ATG start codon, MR20 with size of 1.4 kb containing the middle region of the Ubr1 ORF, and MR19 with size of 2.2 kb containing the C-terminal region of the Ubr1 ORF and 58 bp-3'-UTR covered the full length cDNA ORF. The comparison of the partial sequence of MR23 (4.6 kb insert) with other clones (MR3, MR16, MR20, and MR19) and its sequence search revealed that it contains the C-terminal half of Ubr1 ORF (from aa 2703) flanked in 5'-region by the polyprotein sequence of Friend murine leukemia virus with the orientation reversed, which is believed to be a result from an artifact. Furthermore, the Ubr1 ORF of MR23 was followed by a long 3'-UTR (1010 bp), in which the poly(A) addition site in MR19 was bypassed, the significance of which is unclear.

The resulting mouse Ubr1 cDNA ORF was composed of 5271 bp encoding a 1757-residues (200 kDa) protein, which is largely similar to that (225 kDa) of *S. cerevisiae* UBR1 and the observed molecular weight (180 kDa) of rabbit Ubr1, purified from reticulocyte lysate, on SDS-PAGE (Reiss and Hershko, *J. Biol. Chem* 265: 3685–3690 (1990)). The upstream sequence of the putative (first) ATG start codon, preceded by two in-frame stop codons 48 bp and 93 bp upstream, was largely in an agreement with Kozak's rules (Kozak, M., *J. Biol. Chem.* 266: 19867–19870 (1991)) in that A in position −3 and G in position +4. Immediately downstream of the first ATG codon there are two more ATG codons. Both the second and third ATG codons (the 6th and 12th amino acids in the ORF) have a purine (G and A, respectively) in −3 position and G in +4 position, indication them to be potential alternative start codons. One prominent feature of the N-terminus of the ORF is that among the first 13 residues in ORF 7 are charged (6 negative and 1 positive) amino acids. The meaning of the second and third ATG codons and the highly charged (negative) N-terminal 13 residues are unclear.

iii) Deduced amino acid sequence of mouse Ubr1

Although mouse Ubr1 protein sequence showed relatively low overall homology to *S. cerevisiae* UBR1 (22% identity and 48% similarity) (for *S. cerevisiae* UBR1 sequence see GenBank Accession No. P19812), certain subdomains showed significant homology. More specifically, six specific regions of homology were identified indicating functional relationship of the two proteins. These regions were arbitrarily designated Regions I–VI with designations assigned in order based on location from N-terminus to C-terminus (i.e., Region I is the most C-terminal of the VI regions of homology). Furthermore, comparison of mouse Ubr1 sequence with those available in sequence databases using BLAST programs (Altschul et al., *J. Mol. Biol.* 215: 403–410 (1990)) through the National Center for Biotechnology Information revealed several proteins showing significant homology; a 1927 aa-*Caenorhabditis elegans* ORF (GenBank Accession number U88308) (32% identity and 53% similarity; termed *C. elegans* Ubr1$^2$), a 1872 aa-*S. cerevisiae* ORF (GenBank Accession number Z73196) (21% identity and 47% similarity; termed *S. cerevisiae* UBR2), a 2168aa-*C. elegans* ORF (GenBank Accession number U40029) (21% identity and 45% similarity; termed *C. elegans* Ubr2) and a 794 aa-*Arabidopsis thaliana* CER3 (eceriferum 3; 26% identity and 49% similarity). Besides these proteins, a 147 aa-partial ORF of *Candida albicans* corresponding to the region near N-terminus of mouse Ubr1 (http://alces.med.umn.edu/bin/genelist?LUBR1; termed *C. albicans* UBR1), and a 272 aa-partial ORF of *Schizosaccharomyces pombe* corresponding to the region near C-terminus of mouse Ubr1 (GenBank Accession number M26699; termed *S. pombe* UBR2) also showed significant homologies to the members of UBR1 family. Although the overall homology in these proteins are relatively low (17–32% identity), alignment of their protein sequences revealed several distinctive regions, suggesting that mouse Ubr1 and yeast UBR1, together with their related proteins of previously unknown function, belong to a distinct UBR1 family. The recognition of this fact was made possible exclusively by the isolation and identification of the mouse and human Ubr1 sequences as disclosed herein.

One of the prominent regions of UBR1 proteins is a 66 aa-region (Region I) near N-terminus (in mouse Ubr1), which shows the highest homology among all the regions (61% identity and 75% similarity between mouse Ubr1 and *C. elegans* Ubr1). This region contains a distinctive Cys/His rich domain which does not fit to any other known Cys/His rich motifs. This Cys/His domain is conserved in all the UBR1 family members including mouse Ubr1, *C. elegans* Ubr1, *S. cerevisiae* UBR1, *S. cerevisiae* UBR2, *C. elegans* Ubr2 and a partial N-terminal ORF of *Candida albicans* ORF (http://alces.med.umn.edu/bin/genelist?LUBR1) (termed *C. albicans* UBR1), except *Arabidopsis thaliana* CER3 which contains only Region V and VI. Although this Cys/His structure is likely to be a zinc finger, the number and spacing of Cys and His residues in this structure did not fit to any other known zinc finger. Region V also contains a distinctive Cys/His domain which is conserved in all the UBR1 family members. By comparison of this Cys/His domain with the already known Cys/His structures, the Cys/His domain in Region V was turned out to belong to a RING-H2 finger, a subfamily RING fingers (Borden and Freemont, *Curr Opin Struct Biol* 6: 395–401 (1996)). Several known examples of RING-H2 finger-containing proteins are PSMP, CELG, FAR1, PEP3 and PEP5 (for references of each sequence, see Freemont, P. S., *Ann. NY Acad. Sci.* 684: 174–192 (1993)). One distinctive feature of the RING-H2 of UBR1 family is that the length of loop1 (53 aa–85 aa) is longer than that (12aa–35aa) of those known RING-H2 finger proteins. Other extensive homologies between UBR1 proteins are observed in the 115-aa Region VI (in mouse Ubr1) near C-terminus (24%–50% identity and 46–70% similarity to Region VI of mouse Ubr1). Region VI of *C. elegans* Ubr1 showed highest homology (50% identity and 70% similarity) to that of mouse Ubr1. However, the region VI of *S. cerevisiae* UBR1, the homolog of mouse Ubr1, showed the lowest homology (24% identity and 46% similarity) among UBR1 family members including *S. cerevisiae* UBR2, *C. elegans* Ubr2, *A. thaliana* CER3 and *S. pombe* UBR2. Furthermore, while region VI of all the other related proteins was located 4–14aa from C-terminus of each protein, *S. cerevisiae* UBR1 had an additional 132 and 159 residue-tail which is highly rich in (mainly negative) charged residues (36% and 33%). The significance of the tails is unclear. Region IV also shows high homology in all the UBR1 family members except *C. elegans* UBR2. No protein showed considerable homology to this region when searched using BLAST.

iv) Cloning of Partial Human CDNA and Genomic DNA

To obtain probes for chromosome mapping of human UBR1, a partial human UBR1 CDNA (1 kb), corresponding nt 2218–3227 of mouse Ubr1 cDNA sequence, was cloned by RT-PCR using Poly(A)$^+$ RNA isolated from human 293 cells. The nucleotide and deduced amino acid sequences shared 90% and 93% identities, respectively, with mouse Ubr1 cDNA sequence. Partial human UBR1 genomic DNA fragments (HR8, HR6-4, HR2-25 and HR7-2 with insert sizes of 6.3 kb, 5.8 kb, 3.6 kb and 5.4 kb, respectively, with overlapping of 100–150 bp), corresponding to 1 kb cDNA and ~21 kb genomic DNA, were cloned by genomic PCR using genomic DNA from human 293 cells as a template and the primers based on the human UBR1 cDNA sequence. Partial DNA sequencing of the cloned genomic DNA fragments showed that the ~21 kb genomic DNA region was composed of 11 exons ranging in length from 49 bp to 155 bp. All of the exon/intron junctions contained the consensus GT and AG dinucleotides characteristic of mammalian nuclear pre-mRNA splice sites (Shapiro and Senapathy, *Nucleic Acids Res.* 15: 7155–7174 (1987)).

v) Northern and Southern blot hybridizations of mouse Ubr1 and human UBR1

The expression of mouse Ubr1 and human UBR1 was tested by Northern blot analysis using 2 kb (N-terminal region) or 640 bp (C-terminal region) mouse Ubr1 cDNA fragments for mouse blot and 1 kb-human UBR1 cDNA fragment for human blot. A poly A$^+$ transcript of ~8.0 kb was ubiquitously detected in different mouse tissues using either of the probes (N- or C-terminal region), with relatively high level in skeletal muscle, heart and brain and with lowest level in kidney. The testis-derived Ubr1 mRNA existed as two species: the minor one comigrated with the ~8.0 kb Ubr1 mRNA of the other tissues, while the major one had the apparent size of ~6 kb, which is similar to Northern blot of testis-derived Ntan1 mRNA in which the minor one comigrated with the ~1.4 kb Ntan1 mRNA of the other tissues, while the major one had the apparent size of ~1.1 kb (Grigoryev et al., *J. Biol. Chem.* 271: 28521–28532 (1996)). It is unclear whether the testis specific Ubr1 and Ntan1 Northern patterns were the result of RNA degradation during isolation, specific cleavage of RNA, or two distinct primary transcripts (from different poly(A) addition site or alternative splicing), like $E2_{14K}$ mRNA. The mouse $E2_{14K}$, the mouse homologs of *S. cerevisiae* UBC2 which is a component of the yeast N-end rule, also shows the highest mRNA expression level in skeletal (Grigoryev et al., *J. Biol. Chem.* 271: 28521–28532 (1996)). The upstream region of the rabbit $E2_{14K}$ ORF contains several putative binding sites for MyoD, a muscle-specific transcription factor (Weintraub et al., *Genes Devel.* 5: 1377–1386 (1991)). The human UBR1 mRNA showed similar Northern blot pattern with that of mouse Ubr1.

Southern blotting analysis of mouse or human genomic DNA has revealed rather simple band patterns under either high (final washing; 0.1× SSC/0.1% SDS at 55° C.) or low stringency conditions (final washing; 0.2× SSC/0.1% SDS at 42° C.), suggesting the presence of a single copy of Ubr1 gene in genome and the absence of genes whose structures are closely related to Ubr1 at nucleotide level. However, we cannot exclude the presence of mammalian E3(s) closely related with Ubr1 only at amino acid level. Indeed, several lines of evidences indicate the presence of E3β in rabbit reticulocyte lysates which is believed to be another mammalian ubiquitin-protein ligase recognizing small uncharged N-termini (Ala, Ser, Thr: type III N-terminal destabilizing residues) of the N-end rule (Gonda et al., *J. Biol. Chem.* 264: 16700–16712 (1989)). Although they have different substrate specificities, rabbit Ubr1 and E3β share several properties (Hershko and Ciechanover, *Annu. Rev. Biochem.* 61: 761–807 (1992)). Therefore, it is likely that the sequences of these two proteins are similar.

vi) Interspecific Mouse Backcross Mapping

The mouse chromosomal location of Ubr1 was determined by interspecific backcross analysis using progeny derived from matings of [(C57BL/6J×*Mus spretus*) F$_1$ X C57BL/6J] mice. This interspecific backcross mapping panel has been typed for over 2400 loci that are well distributed among all the autosomes as well as the X chromosome (Copeland and Jenkins, *Trends Genet.* 7: 113–118 (1991)). C57BL/6J and *M. spretus* DNAs were digested with several enzymes and analyzed by Southern blot hybridization for informative restriction fragment length polymorphisms (RFLPs) using a mouse cDNA Ubr1 probe. The 15.0 kb ScaI *M. spretus* RFLP (see *Materials and Methods*) was used to follow the segregation of the Ubr1 locus in backcross mice. The mapping results indicated that Ubr1 is located in the central region of mouse chromosome 2 linked to Thbs1, Epb4.2, and B2m. Although 66 mice were analyzed for every marker and are shown in the segregation analysis, up to 133 mice were typed for some pairs of markers. Each locus was analyzed in pairwise combinations for recombination frequencies using the additional data. The ratios of the total number of mice exhibiting recombinant chromosomes to the total number of mice analyzed for each pair of loci and the most likely gene order are: centromere–Thbs1–4/133–Ubr1–0/113–Epb4.2–1/122–B2m. The recombination frequencies (expressed as genetic distances in centiMorgans (cM)±the standard error) are –Thbs1–3.0±1.5–[Ubr1, Epb4.2]–0.8±0.8–B2m. No recombinants were detected between Ubri and Epb4.2 in 113 animals typed in common suggesting that the two loci are within 2.7 cM of each other (upper 95% confidence limit).

The interspecific map of chromosome 2 was compared with a composite mouse linkage map that reports the map location of many uncloned mouse mutations (provided from Mouse Genome Database, a computerized database maintained at The Jackson Laboratory, Bar Harbor, Me.). Ubr1 mapped in a region of the composite map that lacks mouse mutations with a phenotype that might be expected for an alteration in this locus. The central region of mouse chromosome 2 shares a region of homology with human chromosome 15q. The placement of Ubr1 in this interval in mouse suggests that human homolog will map to 15q, as well.

vii) Chromosomal localization of the human UBR1 locus

The chromosome localization of mouse Ubr1 was independently confirmed and refined by chromosome mapping of human UBR1 by FISH using human UBR1 genomic clones (HR8, HR6-4, HR2-25 and HR7-2) as the hybridization probes. Under the conditions described in *Materials and Methods*, the hybridization efficiency was approximately 91% for these probes (among 100 checked mitotic figures, 91 of them showed signals on one pair of the chromosomes). Since the DAPI banding was used to identify the specific chromosome, the assignment between signal from probes and the long arm of chromosome 15 was obtained. The detailed position was further determined based on the summary from 10 photos. There was no additional locus picked by FISH detection under the condition used, therefore, UBR1 is located at human chromosome 15q15–15q21.1, which is in a good agreement with the result of mouse chromosome mapping of Ubr1.

We claim:

1. An isolated nucleic acid sequence encoding a recognition component of the N-end rule pathway, wherein the nucleic acid sequence hybridizes specifically to the nucleic acid sequence of SEQ ID NO 1 in a hybridization buffer consisting essentially of 50% formamide, 5×SSPE, and 5×Denhardt's solution at a temperature of about 45° C. for a period of hours, followed by repeated washing with 1×SSC at increasing temperatures up to 65° C.

2. An isolated nucleic acid sequence encoding a recognition component of the N-end rule pathway, wherein the nucleic acid sequence hybridizes specifically to the nucleic acid sequence of SEQ ID NO 2 in a hybridization buffer consisting essentially of 50% formamide, 5×SSPE, and 5×Denhardt's solution at a temperature of about 45° C. for a period of hours, followed by repeated washing with 1×SSC at increasing temperatures up to 65° C.

3. A DNA expression vector containing a nucleic acid sequence encoding a recognition component of the N-end rule pathway, wherein the nucleic acid sequence hybridizes specifically to the nucleic acid sequence of SEQ ID NO 1 in a hybridization buffer consisting essentially of 50% formamide, 5×SSPE, and 5×Denhardt's solution at a temperature of about 45° C. for a period of hours, followed by repeated washing with 1×SSC at increasing temperatures up to 65° C.

4. A DNA expression vector containing a nucleic acid sequence encoding a recognition component of the N-end rule pathway, wherein the nucleic acid sequence hybridizes specifically to the nucleic acid sequence of SEQ ID NO 2 in a hybridization buffer consisting essentially of 50% formamide, 5×SSPE, and 5×Denhardt's solution at a temperature of about 45° C. for a period of hours, followed by repeated washing with 1×SSC at increasing temperatures up to 65° C.

5. A cell transformed with a DNA expression vector containing a nucleic acid sequence encoding a recognition component of the N-end rule pathway, wherein the nucleic acid sequence hybridizes specifically to the nucleic acid sequence of SEQ ID NO 1 in a hybridization buffer consisting essentially of 50% formamide, 5×SSPE, and 5×Denhardt's solution at a temperature of about 45° C. for a period of hours, followed by repeated washing with 1×SSC at increasing temperatures up to 65° C.

6. The cell of claim 5 which is a prokaryotic cell.

7. The cell of claim 5 which is a eukaryotic cell.

8. A cell transformed with a DNA expression vector containing a nucleic acid sequence encoding a recognition component of the N-end rule pathway, wherein the nucleic acid sequence hybridizes specifically sequence being characterized by the ability to specifically to the nucleic acid sequence of SEQ ID NO 2 in a hybridization buffer consisting essentially of 50% formamide, 5×SSPE, and 5×Denhardt's solution at a temperature of about 45° C. for a period of hours, followed by repeated washing with 1×SSC at increasing temperatures up to 65° C.

9. The cell of claim 8 which is a prokaryotic cell.

10. The cell of claim 8 which is a eukaryotic cell.

* * * * *

UNITED STATES PATENT AND TRADEMARK OFFICE
CERTIFICATE OF CORRECTION

PATENT NO. : 5,861,312
DATED : January 19, 1999
INVENTOR(S) : Alexander Varshavsky & Yong Tae Kwon It is certified that error appears in the above-indentified patent and that said Letters Patent is hereby corrected as shown below:

In Claim 8, line 9, delete "sequence being characterized by the ability to specifically"

Signed and Sealed this

Twenty-second Day of June, 1999

Attest:

Q. TODD DICKINSON

*Attesting Officer*     *Acting Commissioner of Patents and Trademarks*

UNITED STATES PATENT AND TRADEMARK OFFICE
CERTIFICATE OF CORRECTION

PATENT NO.   : 5,861,312
DATED        : January 19, 1999
INVENTOR(S)  : Alexander Varshavsky & Yong Tae Kwon It is certified that error appears in the above-indentified patent and that said Letters Patent is hereby corrected as shown below:

Applicants request that the following paragraph be introduced as the first paragraph in the referenced patent:

--- This invention was made with government support under Grant #DK 39520 awarded by the National Institutes of Health. The government has certain rights in the invention.---

Signed and Sealed this

Seventh Day of September, 1999

Attest:

Attesting Officer

Q. TODD DICKINSON

Acting Commissioner of Patents and Trademarks